United States Patent [19]
McCormack et al.

[11] Patent Number: 5,472,868
[45] Date of Patent: Dec. 5, 1995

[54] STABLE RABBIT-MOUSE FUSION PARTNER

[75] Inventors: Robert T. McCormack; Ru-shya Liu, San Diego, both of Calif.; Joseph V. Manetta, Indianapolis, Ind.; John R. Sportsman, Palo Alto, Calif.

[73] Assignee: Eli Lilly & Company, Indianapolis, Ind.

[21] Appl. No.: 230,432

[22] Filed: Apr. 19, 1994

Related U.S. Application Data

[63] Continuation of Ser. No. 932,627, Aug. 20, 1992.

[51] Int. Cl.$^6$ ............................... C12N 5/26; C12N 5/20
[52] U.S. Cl. .................... 435/240.26; 435/172.2; 435/70.2
[58] Field of Search .................. 435/70.21, 240.27, 435/172.2, 70.2, 240.26; 530/387.3, 388.1, 388.24, 399, 416, 809, 420; 935/96, 102, 104

[56] References Cited

U.S. PATENT DOCUMENTS

| | | |
|---|---|---|
| 3,811,840 | 5/1974 | Bauer et al. . |
| 4,246,339 | 1/1981 | Cole et al. . |
| 4,366,241 | 12/1982 | Tom et al. . |
| 4,371,462 | 2/1983 | Hecht ................................. 260/112 R |
| 4,407,943 | 10/1983 | Cole et al. . |
| 4,440,301 | 4/1984 | Intengan . |
| 4,496,654 | 1/1985 | Katz et al. . |
| 4,533,496 | 8/1985 | Lewis et al. ........................ 260/112 R |
| 4,632,901 | 12/1986 | Valkirs et al. . |
| 4,634,664 | 1/1987 | Oestberg . |
| 4,704,255 | 11/1987 | Jolley . |
| 4,727,019 | 2/1988 | Valkirs et al. . |
| 4,740,468 | 4/1988 | Weng et al. . |
| 4,747,019 | 5/1988 | Ito et al. . |
| 4,842,998 | 6/1989 | Meng et al. . |
| 4,859,595 | 8/1989 | Strosberg et al. . |
| 4,916,056 | 4/1990 | Brown et al. . |
| 4,977,081 | 12/1990 | Raybould et al. . |

FOREIGN PATENT DOCUMENTS

| | | |
|---|---|---|
| 0186100 | 7/1986 | European Pat. Off. . |
| 0217403 | 4/1987 | European Pat. Off. . |
| 349851 | 10/1990 | European Pat. Off. .......... C12N 5/16 |

OTHER PUBLICATIONS

Groves et al. (1989) Vet. Immunol. Immunopath. 23:174.
Harlow et al. (1988) "Antibodies: a Laboratory Manual," Cold Spring Harbor Press, Cold Spring Harbor, N.Y. p. 271.
"The Merck Index", atn. ed. (Windholg et al, eds.) Marck & Co., Inc., Rahway N.J. 1976, p. 7290.
D. Groves et al., "The Production and application of non-rodent monoclonal antibodies in veterinary science.", *Veterinary Immunology And Immunopathology*, Nov. 1989, vol. 23, No. 1–2, pp. 1–14.
M. Suter et al., "Rabbit single domain antibodies specific to protein C expressed in prokaryotes.", *Immunology Letters*, Jul. 1992, vol. 33, No. 1, 2, pp. 53–59.
Anderson, et al. Clin. Chem. 32(9): 1692–1695 (1986).
Clezardin, et al., J. of Chromatography 319: 67–77 (1985).
Collins, et al. Proc. Natl. Acad. Sci. (USA) 71(2): 260–262 (1974).

(List continued on next page.)

*Primary Examiner*—Margaret Parr
*Assistant Examiner*—Jacqueline G. Krikorian
*Attorney, Agent, or Firm*—Knobbe, Martens, Olson and Bear

[57] ABSTRACT

A stable xenogeneic fusion partner that is a product of the fusion of a mouse myeloma cell and a non-transformed rabbit partner cell. The fusion partner produces undetectable levels of antibody, as determined by an enzyme linked immunosorbent assay. A method for generating rabbit monoclonal antibodies is disclosed that comprises fusing a non-transformed rabbit partner cell with a rodent myeloma cell to produce a xenogeneic fusion partner, selecting a stable fusion partner producing undetectable levels of antibodies, fusing the stable fusion partner with a rabbit antibody producing cell and isolating an antibody producing cell line that produces antibodies directed to a predetermined antigen.

1 Claim, 9 Drawing Sheets

OTHER PUBLICATIONS

Dreher, et al., J. of Immunology 130(1): 442–448 (1983).
Flynn, et al. J. of Immunological Methods 121: 237–246 (1989).
James, et al., J. of Immunological Methods 100: 5–40 (1987).
Kennedy, et al. J. Gen. Virol 69: 3023–3032 (1988).
Klein, J. *Immunology The Science of Self–Nonself Discrimination.* p. 251 (1982).
Lindmo, et al. J. of Immunological Methods 72: 77–89 (1984).
Nakamura, Robert. "General Principles of Immunoassays" *Immunochemical Assays and Biosensor Technology for the 1990s:* 3–21 (1992).
Osterland, et al., J. Exp. Med. 123: 599–614 (1966).
Raybould, et al. Science 240: 1788–1790 (1988).
Tasaka, et al. Acta Histochem. Cytochem. 17(3): 283–286 (1984).
Teng, et al. Proc. Natl. Acad. Sci. (USA) 80: 7308–7312 (1988).
Valkirs, G. Laboratory Medicine 19(9): 564–567 (1988).
Waldmann, et al. Science 252: 1657–1662 (1991).
Ware, et al. J. of Immunological Methods 85: 353–361 (1985).
Ichimori, et al. Biochem. and Biophy. Res. Commun. 129(1): 26–33 (1985).
Iizasa, et al. Hybridoma 9(3): 211–219 (1990).
Ostberg, et al. Hybridoma 2(4): 361–367 (1983).
Posner, et al. Hybridoma 6(6): 611–625 (1987).
Sugiyama, et al. Hybridoma 10(1): 11–19 (1991).

Ka = 2.74±0.64 E9
Corr = 0.804

STABLE RABBIT-MOUSE FUSION PARTNER

This application is a continuation of application Ser. No. 07/932,627, filed Aug. 20, 1992.

FIELD OF THE INVENTION

The present invention relates generally to the field of monoclonal antibodies. More specifically, the invention relates to methods for producing rabbit monoclonal antibodies and to the cells used to produce them.

BACKGROUND OF THE INVENTION

Monoclonal antibodies are typically produced by fusing an antibody producing cell with an immortalizing cell to generate a homogenous population of cells all producing antibodies directed to the same antigenic epitope. Mice and rats are traditional sources for the antibody producing cells. Cell hybrids produced from the fusion of the antibody producing cell and the immortal fusion partner, termed fusion products of hybrids, are selected and tested for the quality and quantity of secreted antibodies reacting with the immunizing antigen. The hybrids are expanded in vitro or in vivo, as ascites for large scale antibody production. For a review of current procedures used to develop monoclonal antibodies, see Waldman, T., *Science* 252:1657–1662 (1991) and Harlow, et al., *Antibodies: A Laboratory Manual.* Cold Spring Harbor, 1988. New York.

Monoclonal antibodies are preferred over polyclonal antibodies for diagnostic assays. Monoclonal antibodies represent a homogenous population of antibody with a defined specificity. The antibody can be used repeatedly over time with consistent results. Since the monoclonal population is homogenous it tends to have a more predictable reaction pattern in immunoassays over its polyclonal counterpart. Moreover, in contrast to polyclonal antibodies, monoclonal antibodies of consistent quality can be generated over a prolonged period. The specificity of monoclonal antibodies makes them the preferred type of antibody for immunoassays such as enzyme linked immunosorbent assays (ELISA), radioimmunoassays (RIA), western blot or immunohistochemical assays.

While rats and mice are the typical sources for monoclonal antibody production, some antigens do not sufficiently stimulate the development of high-affinity antibodies in mice and rats to make them useful in diagnostic assays. Examples of this type of antigen primarily include carbohydrate moieties. While amino acid epitopes tend to be more immunogenic than carbohydrates, there are amino acid epitopes that do not stimulate high affinity antibodies in rodents. Therefore another convenient source of monoclonal antibodies would be of great benefit to the art.

Rabbits are an excellent source of polyclonal antibodies. Antigen stimulation, in rabbits, using a wide variety of immunogens, consistently generates high titer rabbit polyclonal antibodies. Moreover, rabbits are a common and convenient laboratory animal. While rodents are less likely to produce high-affinity antibody to carbohydrate moieties, rabbits more consistently react positively to foreign carbohydrate determinants. The difference in affinity between rabbits and mice may be attributed to the fact that these organisms are evolutionarily disparate and may therefore respond differently to the same antigen. Thus rabbits may be better able to generate stronger antibody responses to those human epitopes that are weakly reactive in mice. Carbohydrate determinants are important markers for cancer diagnosis and infectious disease; thus there is an increasing need for high affinity antibodies to these antigens.

In addition to the different antigenic responses between rabbit and mice, antibodies produced in rabbits offers additional advantages to diagnostic assays. Some humans, for example, tend to have endogenous levels of anti-murine antibodies (HAMA). In standard ELISA assays that employ two murine antibodies, this antibody cross-links the two murine antibodies to generate false positive signals. Reduced false positives are an important goal in immunoassay development. Therefore mechanisms to reduce false positives in diagnostic assays are important to health care personnel. Endogenous human anti-rabbit antibodies are uncommon. Additionally, human anti-mouse antibodies may complicate therapeutic uses for murine antibodies as well. For example, the ability to detect an antigen associated with cancer in an individual who is imaged or treated with murine monoclonal antibodies to that same antigen may be compromised in a diagnostic assay that employs the murine monoclonal-monoclonal format. A rabbit-rabbit double monoclonal format or a rabbit monoclonal-murine monoclonal format would obviate the need for a mouse-mouse monoclonal format.

While monoclonal antibodies are generally preferred over polyclonal antibodies in immunoassays, there is no efficient method available to produce rabbit monoclonal antibodies in a consistent quantity or quality. There are no rabbit myelomas or suitable immortalizing fusion partners derived from rabbits. Other methods for producing rabbit monoclonal antibodies include B cell transformation in rabbits using SV40 (simian virus 40) or EBV (Epstein Barr Virus) and oncogene transfection. All of these methods have proven difficult and results are inconsistent (see Collins, et al., *Proc. Natl. Acad. Sci.* 71:260–262, 1974 and Strosberg, et al., U.S. Pat. No. 4,859,595, issued Aug. 22, 1989). In the absence of a rabbit-derived myeloma cell line, standard monoclonal antibody techniques are not useful. Thus, at present there is no reproducible method for generating rabbit monoclonal antibodies.

Some laboratories have looked at the production of heterohybrids. Antibody-secreting cells isolated from one species and fused with immortalizing cells from another species yield interspecies, or heterohybridomas. The term heterohybrid fusion is used herein interchangeably with xenogeneic fusions. Raybould, et al. disclose a method for producing rabbit-mouse hybridomas that secrete rabbit monoclonal antibodies (Raybould, et al., *Science* 240:1788–1790, 1988 and Raybould, et al., U.S. Pat. No. 4,977,081, issued Dec. 11, 1990). Rabbit monoclonal antibodies were produced by fusing mouse myeloma cells with rabbit splenocytes. Stable antibody production was only obtained when the fusion products were grown in the presence of rabbit serum. Raybould, et al. indicate in their conclusions that the use of rabbit serum is essential to rabbit monoclonal antibody production.

Rabbit monoclonal antibodies produced in the presence of rabbit serum is contaminated by endogenous rabbit antibodies present in the sera. Rabbit sera contains between 10–30 mg/ml of immunoglobulin G (IgG) as compared with microgram quantities of IgG produced by a murine hybridoma or heterohybridoma. Nonspecific rabbit immunoglobulin present in the monoclonal antibody preparation increases background reactivity and reduces the sensitivity of assays designed to detect antibody production from the fusion product. To prepare monoclonal antibodies for diagnostic assays, the monoclonal antibodies must be purified away from the nonspecific rabbit immunoglobulin present in the sera. These techniques are difficult, labor intensive and increase production costs.

Antibodies produced from interspecies hybridomas such as those methods disclosed by Raybould, et al. tend to be unstable. Because of the abnormal number of chromosomes, segregation does not always deliver identical sets of chromosomes to daughter cells and these chromosomes may be lost. Both the chromosomes containing the functional, rearranged immunoglobulin heavy-chain and light-chain genes and the chromosomes permitting drug resistance are needed to maintain cell replication and antibody production. As disclosed in the detailed description of the invention, (see Tables 2 and 3) the interspecies fusion of Raybould was unstable over time and failed to produce antibody.

The commercial use of a monoclonal antibody depends on the stability and quality of antibodies produced from a particular clone. In addition to stability and quality, the concentration of antibodies produced from the clone should be high enough, preferably greater than 25 µg/ml, to obtain commercially useful quantities of antibodies. Usually the highest levels of antibody production are obtained when the antibodies are produced as ascites. Ascites production is the most cost effective and efficient way to grow large quantities of antibodies. Normally murine hybridomas are produced as ascites in a closely related murine host. Heterohybridomas secrete antibodies derived from an animal other than a mouse. An immunocompetent mouse will see the heterohybridomas as foreign or develop an immune response to the antibodies. Thus a method for producing rabbit monoclonal antibodies as ascites would represent a significant advance in the art.

While there is some evidence that rabbit heavy chain-murine light chain chimeric antibodies can be produced as ascites in nude mice, the use of mice to generate antibodies comprised of rabbit light and rabbit heavy chain is heretofore undisclosed (Dreher, et al., *J. Immunology* 130:442–447, 1983). Moreover, neither the chimeric clones nor those disclosed by Raybould were stable over time. Therefore useful quantities of antibodies for commercial diagnostic assays could not be produced. Ware, et al. demonstrated that rat X mouse hybridomas can be grown in severe combined immunodeficient (SCID) mice. (*J. Immunological Methods* 85:353–361, 1985, hereby incorporated by reference). Antibody production for xenogeneic fusions was previously limited to antibody production in tissue culture. The demonstration of high level heterohybridoma rabbit antibody production in SCID mice is heretofore undisclosed.

The ability to consistently produce rabbit monoclonal antibodies is undisclosed. Further, a method for reproducibly generating rabbit monoclonal antibodies in the absence of rabbit serum and a method for growing the antibody producing cells as an ascites tumor would be a significant advancement in the art. Rabbit monoclonal antibodies could thus be used to overcome some of the difficulties associated with generating antibodies to carbohydrate (Raybould, et al., supra).

SUMMARY OF THE INVENTION

The present invention discloses a stable xenogeneic fusion partner comprising the product of a cell fusion between a rodent myeloma cell and a non-transformed rabbit cell. In one preferred embodiment of the invention, the stable fusion partner produces undetectable levels of antibody. The rodent myeloma cell is preferably mouse derived and in a particularly preferred embodiment of this invention, the mouse-derived rodent myeloma cell is the SP2/0 cell line. In another particularly preferred embodiment of this invention, the stable fusion partner is derived from a fusion between an SP2/0 cell and bovine somatotropin sensitized rabbit splenocytes. This fusion partner is hypoxanthine-aminopterin-thymine sensitive and hypoxanthine-guanine-phosphoribosyl transferase deficient. Naturally occurring variants and mutants of this stable fusion partner are additionally contemplated within the scope of this invention. In yet another particularly preferred embodiment of this invention, the stable fusion partner comprises the cell line deposited with the American Type Culture Collection (Rockville, Maryland), under the Budapest Treaty, as culture number 11086. This stable rabbit-mouse fusion partner cell line was deposited at the American Type Culture Collection, located at 12301 Parklawn Dr., Rockville, Md. 20852 USA, on Jul. 22, 1992, and is available from the American Type Culture Collection under accession number CRL 11086.

In another preferred embodiment of this invention, a stable cell line that secretes rabbit monoclonal antibodies is contemplated. This stable cell line comprises the product of the fusion of a stable xenogeneic fusion partner which in turn comprises the fusion of a rodent myeloma cell and a non-transformed rabbit cell with a rabbit splenocyte that has been sensitized with a predetermined antigen and produces antibodies to that antigen. Preferably, this stable cell line is the product of a fusion that utilizes a stable xenogeneic fusion partner that itself does not secrete detectable quantities of antibodies. In addition, this stable cell line is preferably the product of a fusion wherein the stable xenogeneic fusion partner is in turn the product of a fusion that utilized a mouse-derived rodent myeloma cell. More preferably, the cell line is the product of a fusion that utilized an SP2/0 murine myeloma cell line and more preferably, the rabbit splenocytes were sensitized with a carbohydrate antigen and these splenocytes produced antibodies to that antigen. In a preferred embodiment, the stable xenogeneic fusion partner is the cell line deposited with the American Type Culture Collection as cell culture number 11086. In a particular preferred embodiment, the rabbit splenocytes were sensitized with N-acetyl D-glucosamine and produced antibodies to the carbohydrate antigen.

In yet another preferred embodiment, a method is provided for producing rabbit monoclonal antibodies comprising the steps of fusing a nontransformed rabbit partner cell with a rodent myeloma cell to produce a xenogeneic fusion partner, selecting a stable fusion partner producing undetectable levels of antibody, fusing the stable fusion partner with a rabbit antibody-producing cell and isolating an antibody producing cell line obtained from the fusing step that produces antibodies directed to a predetermined antigen. In one embodiment, the selecting step additionally comprises generating a drug resistant stable fusion partner and the isolating step additionally comprises growing the antibody producing cell in the drug. Preferably, the rodent myeloma cell is mouse derived and the rabbit antibody producing cell is obtained from a rabbit immunized with the predetermined antigen. In a preferred embodiment of this method, the stable fusion partner is the cell line deposited with the American Type Culture Collection as culture number 11086.

In another preferred method for producing rabbit monoclonal antibodies, a stable fusion partner derived from a fusion between a SP2/0 cells and bovine somatotropin-sensitized rabbit splenocytes is hypoxanthine-aminopterin-thymidine sensitive and hypoxanthine-guanine-phosphoribosyl transferase deficient. The method comprises fusing the stable fusion partner with rabbit antibody-producing cells, isolating the fusion products, growing the fusion products and collecting antibodies from the fusion products. In one embodiment the growing step occurs in vitro and in a preferred embodiment the growing step occurs in vivo. Preferably, the in vivo growing step consists of generating ascites and more preferably, the growing step consists of introducing the fusion products into mice deficient in mature T and B lymphocytes.

DETAILED DESCRIPTION OF THE INVENTION

Figure 1:
FIG. 1 is a photograph of a chromosome spread of metaphase chromosomes from the exemplary fusion partner cell line OMB-037. The arrows identify rabbit chromosomes. Acrocentric chromosomes are murine.

Using methods disclosed herein, the generation of rabbit monoclonal antibodies is now possible through the employ of a stable, productive xenogeneic fusion partner. The term xenogeneic fusion partner is used to describe the interspecies fusion of two or more cells to obtain an immortal cell line capable of fusing with spleen cells. Stable, xenogeneic fusion partner cell lines derived in part from rabbit cells are required for the reproducible production of rabbit monoclonal antibodies.

The reproducible production of rabbit monoclonal antibodies is undisclosed in the art. The use of xenogeneic fusion partners involving more than the fusion of two cells is disclosed for a few systems, but not for rabbits. In particular Oestberg, et al., (U.S. Pat. No. 4,634,664, issued Jan. 6, 1987 and Teng, et al. (*Proc. Natl. Acad. Sci.* (USA) 80:7308–7312, 1983) disclose the use of xenogeneic fusion partners to produce human monoclonal antibodies. Xenogeneic fusion partners are also described for the production of bovine and sheep monoclonal antibodies; however ascites production is neither disclosed nor described (Kennedy, et al., *J. Gen. Virol.* 69:3023–3032, 1988, and Flynn, et al., *J. Immunol. Methods* 121:237–246, 1989).

Success in human and large mammalian systems is not predictive of success in rabbits. The fusion of a myeloma cell with a host partner cell does not, of itself, guarantee success in generating a useful xenogeneic fusion partner. A useful xenogeneic fusion partner preferably exhibits cell stability over time and preferably replicates with a doubling time of at least 24 hours. Moreover, the cells are preferably sensitive to Hypoxanthine, Aminopterin and Thymidine (HAT). More preferably, the fusion partner contains at least one host species-specific chromosome. While it is recognized that not all fusion partners obtained by this method will be equally suited as fusion partners, methods are detailed for the testing and isolation of stable fusion partners well suited for fusion. The selection of a suitable fusion partner as disclosed herein facilitates the reproducible and consistent production of monoclonal antibodies. Therefore, methods are disclosed for selecting a suitable xenogeneic fusion partner useful for preparing rabbit monoclonal antibodies, for testing the fusion partner and for using the fusion partner in subsequent fusions to produce high quality and useful quantities of rabbit monoclonal antibodies. In addition, an exemplary xenogeneic fusion partner OMB 037, obtained using the methods outlined in this invention is deposited under the terms of the Budapest Treaty as of Jul. 22, 1992. in the American Type Culture collection, 12301 Parklawn Dr., Rockville, Md. 20852 (ATCC) as CRL 11086.

The production and identification of a suitable fusion partner is essential to the production of monoclonal antibodies obtained from xenogeneic fusions. Xenogeneic fusions of mouse or rat myeloma (or other rodent immortalizing cells) with splenocytes or other cells from a different species produces cells that are often genetically unstable. Chromosomes are deleted from the cells with further cell passage in culture. Thus, the fusion product of a mouse myeloma with splenocytes derived from another immunized animal may initially secrete antibody. Over time, chromosome loss may result in the loss of antibody expression. As disclosed by Raybould, et al., media components such as species specific sera or additional additives may be required to maintain these cell lines. Thus, for many xenogeneic fusions of a myeloma and a splenocyte derived from a different species, antibody production is not stable over time.

GENERATION AND SELECTION OF A SUITABLE FUSION PARTNER

In a preferred embodiment of this invention, a stable xenogeneic fusion partner is produced by fusing a rodent myeloma cell with a non-transformed rabbit partner cell. It is contemplated within the scope of this invention that either rat or mouse myeloma cells may be used in practicing this invention. Myeloma cells are immortalized plasma cells and there are a variety of myeloma cells used in the art. Some, like the mouse myeloma cell line SP2/0, are a fusion product of a murine cell line P3 and murine splenocytes. Other myeloma cells secrete or produce light chain antibody protein. There are a number of mouse immortalizing cell lines known in the art that are suitable for fusion with splenocytes. Possible mouse myeloma cell lines that may be used in this invention include, but are not limited to, IgG secreting mouse myeloma cells such as MOPC 21 or P3X63AG8 (ATCC #T1B9) and more preferably, non-antibody secreting cells such as SP2/0 (ATCC #CRL 1581), NS-1 (ATCC #TIB18), P3.X63AG8.653 (ATCC #CRL 1580), F0, S194/5.XXO.BU-1 (ATCC #CRL 1580) and FOX-NY (ATCC #CRL 1732). These cell lines are available from ATCC (Rockville, Md.). The following examples used SP2/0 as the immortalizing cell since the cell line is well characterized in the art and does not secrete antibody light or heavy chain protein. For a history of the SP2/0 cell lineage and its relationship to other myelomas, see Harlow, et al. 1988 (*Antibodies: A Laboratory Manual* p.145).

It is contemplated within the scope of this invention that at least one rabbit chromosome or genes translocated from at least one rabbit chromosome onto an immortalized cell chromosome is required for the production of a useful immortalizing fusion partner. Thus, candidates for an immortalizing fusion partner could include immortalizing cell derivatives from any number of species, such as human, mouse, goat or the like. This immortalizing fusion partner is then fused to a rabbit antibody producing cell. However, others believe that chromosome translocations of essential portions of the rabbit chromosome that permit rabbit immunoglobulin expression are sufficient for rabbit antibody production. Thus, the identification of rabbit chromosomes per se is not an accurate predictor for fusion partner selection.

The non-transformed partner cell used in the fusion is a growth regulated cell, of the B cell lineage, derived from a rabbit. In a preferred embodiment of this invention, the cell is a rabbit splenocyte. Example 1 details the generation of a xenogeneic fusion partner that is the product of a fusion between rabbit splenocytes obtained from a rabbit immunized with bovine somatotropin. Bovine somatotropin is an exemplary immunogen. Therefore it is contemplated that another immunogen could be used to obtain an immune response in the rabbit donor used to generate the fusion partner. It is further contemplated within the scope of this invention that the splenocytes used in a fusion with mouse myeloma cells to obtain the fusion partner, need not be derived from an immunized rabbit since immunization is not a prerequisite for the identification of a suitable xenogeneic partner.

Cell fusion between the immortalizing cell and the non-transformed rabbit partner cell may be performed using a number of methods known in the art. Chemicals that promote fusion are commonly referred to as fusogens. These agents are extremely hydrophilic and facilitate membrane contact. As one method of cell fusion, the cells are fused using polyethylene glycol. In a preferred embodiment the methods for cell fusion follow those described in Example 5 and in the section entitled "Fusion of Stable Fusion Partner with Rabbit Splenocytes". A specific example of the method used to generate an exemplary fusion partner, OMB-037, is provided in Example 1.

Other methods that could similarly be used to facilitate cell fusion include electrofusion. In this method, cells are placed in special buffers and are exposed to a predetermined electrical discharge that alters the cell membrane potential and increases the likelihood of cell fusion. Additional methods for cell fusion contemplated for use in this invention are bridged-fusion methods or the like. As one example of a bridged-fusion method, the antigen is biotinylated and the myelomas are avidinylated. When the cells are added together, an antigen reactive B cell-antigen-biotin-avidin-myeloma bridge is formed. This permits the specific fusion of an antigen reactive cell with an immortalizing cell. The method may additionally employ chemical or electrical means to facilitate cell fusion.

The fusion products are grown in a compatible media as outlined for the xenogeneic fusion of Example 1. As in Example 1, following fusion, the cells are selected for hypoxanthine aminopterin and thymidine (HAT) sensitivity. Preferably, the fusion products do not produce antibody. If the non-transformed rabbit cells were derived from rabbit splenocytes, and in particular from rabbit splenocytes obtained from an immunized rabbit, then it is necessary to check the cell supernatants for antibody production, including production of either light or heavy antibody chains. As one method for selecting fusion products that are HAT resistent and do not secrete antibody, the supernatant from fusion products sensitive to HAT and 8-azaguanine resistant are tested for the presence of IgG using standard ELISAs well known in the art. The supernatant is additionally electrophoresed using cellulose acetate or polyacrylamide gel electrophoresis to visualize antibody protein. Finally, cell lysates from the fusion products are tested for IgG specific mRNA. Cells testing negative for IgG production are tested for their efficacy as a fusion partner.

Useful candidates for xenogeneic fusion are those fusion products that double preferably at least once in 24 hours, fail to produce antibody protein and are capable of becoming 8-azaguanine resistant. A method for making a candidate fusion partner 8-azaguanine resistant is provided in Example 3. As an alternative to 8-azaguanine resistance, the cells can also be made 5BUdR (5-bromodeoxyuridine) resistant. Such methods are available in general procedural texts for monoclonal antibody production, including *Antibodies: A Laboratory Manual* (Harlow, et al., supra). Other selectable drugs suitable for selecting fusion products are known in the art. For an overview of other selection systems see Klein, J. (1982) in *Immunology: The Science of Self-Nonself Discrimination.* J. Wiley & Sons, New York.

As an example of the development and selection of a stable fusion partner suitable for the production of rabbit monoclonal antibodies, the fusion partner OMB-037 was selected from splenocytes obtained from a rabbit immunized with bovine somatotropin using the immunization protocol provided in Example 1 and fused to mouse myeloma cell line SP2/0.

The resulting fusion partner was tested for antibody secretion, growth characteristics and by karyotyping. The fusion partner was tested in subsequent rabbit splenocyte fusions and tested for rabbit monoclonal antibody production. A photograph of a chromosome spread of the fusion partner cell line OMB-037 is provided in FIG. 1. Rabbit chromosomes are identified by arrows. Mice have 44 chromosomes that are acrocentric while rabbit cells have 40 chromosomes that are metacentric. Originally the cell line contained 6–8 rabbit chromosomes and this number of chromosomes was constant for 9 months of continuous culture. After approximately one year in culture the cell line contained one rabbit chromosome. Despite this chromosome loss over time, the cells functioned efficiently as fusion partners and the monoclonal antibody producing cells generated by fusing the xenogeneic fusion partner with an antibody producing cell have been stable in culture over one year. To ensure a constant fusion efficiency, the xenogeneic fusion partner was initially expanded and frozen down. A new frozen aliquot was used each 6 months. A protocol for the long term use of a suitable xenogeneic fusion partner is provided in Example 2. Even though the karyotype for OMB-037 changes slightly overtime, new batches thawed each 6 months ensured consistent fusions.

GENERATION OF STABLE MONOCLONAL ANTIBODY PRODUCING CELLS

To generate rabbit monoclonal antibodies, the stable fusion partner was fused to cells producing rabbit antibodies. Potentially any cell producing rabbit antibodies could be used in a fusion with the xenogeneic fusion partner. Rabbit antibody producing cells were obtained by immunizing rabbits with antigen of choice using methods well known in the art. For a review of rabbit immunization strategies see Harlow, et al. (supra, pp 92–114).

In general, immunogens must fulfill two criteria to be immunogenic. First, they must possess a site for antibody binding and second, they must possess a site for class II/T cell interaction. Therefore, most foreign protein fulfill these criteria and are immunogenic. Immunization of rabbits with carbohydrate groups bound to protein or carbohydrate alone can be used to initiate an immune response. In general, better immunogenic responses are obtained by immunizing rabbits with carbohydrate groups associated with protein. As an example of the ability of the fusion partner to facilitate rabbit monoclonal antibody production and specifically to produce monoclonal antibodies to carbohydrate moieties, the exemplary fusion partner OMB-037 was fused with splenocytes from rabbits immunized with pepsin-digested Group A Streptococcus (GAS).

In Example 4, outlined below, pepsin-digested Group A *Streptococcus pyrogens* (cell wall removed) was used to initiate an immune response. Purified preparations of Group A Streptococcus-specific epitope (N-acetyl glucosamine) were not used since nitrous acid extract enriched fractions of N-acetyl glucosamine (NAG) would likely paralyze the immunized animal. It is well known in the art that high affinity monoclonal antibodies directed to this epitope are difficult to develop in mice.

Strategies for immunization with polypeptide are well documented in the art. Generally, animals are initially immunized by introducing the antigen in combination with an adjuvant such as Freunds (see Harlow, et al., supra.). Other adjuvants are additionally described in the art. Subsequent boosting injections of antigen are given in association with incomplete Freunds adjuvant, with another adjuvant known in the art or alone, without adjuvant. Usually, animals are given an initial injection. Two to four weeks later, when the immunoglobin response has developed and secreted antibodies have cleared, boosting injections are given to develop an IgG response.

Strategies for immunizing against carbohydrate are different. One strategy suitable for carbohydrate immunization and particularly suited for Group A Streptococcus is provided in Example 4 and adapted from Osterland, et al. (*J. Exp. Med.* 123:599–614, 1966 hereby incorporated by reference). The rabbits were tested three weeks into the immunization protocol. Adequate titers were usually achieved within this time frame. If not, rabbits were intravenously given boosts of antigen every other week (IV), with the largest dose of antigen, until acceptable titers were measured. Modifications of the protocol provided in Example 4 and other immunization protocols could additionally be used to generate useful antibody titers.

It is additionally contemplated within the scope of this invention, that rabbit cells may be immunized in vitro. Procedures are available for immunizing human lymphocytes in culture. For a review of in vitro immunization techniques, see James, et al. (*J. Immunol. Methods* 100:5–40, 1987, hereby incorporated by reference).

FUSION OF STABLE FUSION PARTNER WITH RABBIT SPLENOCYTES

Rabbits are immunized with antigen according to the method described above or other methods known in the art. Rabbits containing suitable antibody titers, preferably within the range of 2–3 times greater than preimmunized sera from the same rabbit, to the antigen of interest are selected for use. In Example 4, below, the selected rabbit was boosted a final time with Group A Streptococcus (GAS) antigen three days before fusion.

Methods for obtaining and preparing single cell suspensions of rabbit splenocytes for cell fusion are readily available in the literature. The methods used here were similar to those used to generate mouse splenocytes. Briefly, the rabbit was sacrificed and the spleen was physically teased and resuspended in a suitable media such as phosphate buffered saline or HB-GRO media (Irvine Scientific, Santa Ana, Calif.). Cell concentrations were determined using methods well known in the art and the concentration was adjusted to $2.5 \times 10^6$ cells/ml. Leu-leu-ome peptide (L-Leucyl-L-leucine-methyl ester, Boehringer Mannheim, Indianapolis, Ind.) was added to kill the lysosomal-enriched cells such as macrophages. The cells were spun down and mixed with the fusion partner.

There are many methods known in the art to facilitate cell fusion for hybridoma production. Polyethylene glycol (PEG) is the standard fusion-mediating agent. Cell ratios of splenocytes to fusion partner cells will be optimized for the conditions of each particular fusion. Cell to fusion partner ratios traditionally vary between 2:1 to 10:1. Similarly, the optimal concentrations of PEG will vary depending on the molecular mass of the PEG. In Example 5, below, 35% PEG 1500 was selected, however other concentrations of other molecular mass PEG, such as 50% PEG 4000, could alternatively be used to facilitate cell fusion.

It is important to maximize fusion efficiencies, particularly for epitopes that do not readily generate an immune response, such as carbohydrate. The fusion partner and the culture media are two of the most important variables in obtaining good fusion efficiencies in the instant fusions. To reduce the risk that rabbit antibody producing cells go undetected, fusion efficiencies should approach 100%; in other words, growth in all of the tissue culture wells containing cells. U.S. Pat. No. 4,977,081 to Raybould, et al. teach the production of rabbit monoclonal antibodies through the fusion of a mouse immortalizing cell with rabbit splenocytes in the presence of rabbit serum. Moreover, Raybould, et al. indicate that normal rabbit serum is required for rabbit monoclonal antibody production.

The rabbit monoclonal antibody procedure of Raybould was compared to other fusion combinations and conditions. In a study to determine the optimal combination of fusion partner and media conditions, a fusion partner, OMB-037, obtained using the methods of this invention, was compared with murine myeloma fusion partners SP2/0 and P3,653. Rabbit serum supplemented media (RS), horse serum (HS), fetal calf serum (FCS) and spleen-conditioned medium (SCM) were compared in combination with the fusion partners. Spleen conditioned media was harvested as supernatant from normal splenocytes seeded at $1 \times 10^6$ cells/ml. in spinner cultures and cultured for 48 h in standard medium (HB-GRO). Cultures were used at a final concentration of 20%.

Figure 2:
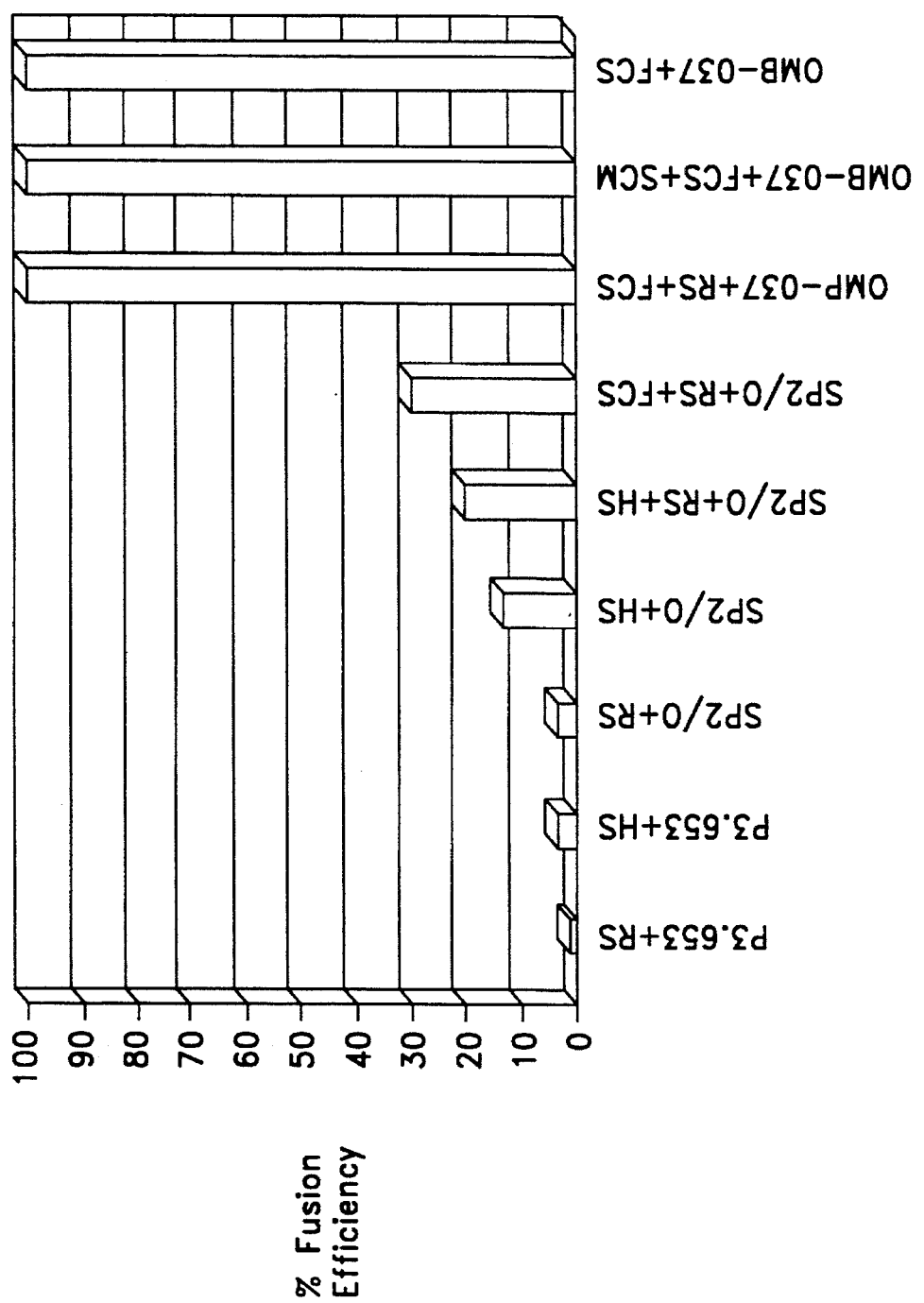
FIG. 2 illustrates the results of a study to optimize the fusion efficiency of rabbit monoclonal antibody production. The culture conditions are provided on the horizontal axis. P3.653, SP2/0 and OMB-037 fusion partners were tested together with different sera: rabbit sera (RS), horse sera (HS), fetal calf (FCS) and splenocyte conditioned media (SCM). The percentage fusion efficiency is expressed as the number of wells with viable hybrids divided by the total number of wells receiving hybrids in each group.

The fusions were performed as described in Example 5 except that rabbit splenocytes were obtained from a non-immunized animal. The culture condition modifications tested are denoted on the horizontal axis of FIG. 2. Raybould's combination is identified by an arrow. As exemplified by FIG. 2, the best fusion efficiencies were obtained using fusion partner OMB-037. In contrast to Raybould, optimal fusion efficiencies were not dependent on the presence of rabbit serum. Results are expressed as the number of wells containing viable hybrids relative to the number of wells plated for each sample. A minimum of 288 wells were used for each sample group. Fusion products were identified in the wells by their size and the presence of cell growth in the wells. These methods provide an exemplary strategy for testing fusion efficiency in cell fusions selected for the production of rabbit monoclonal antibodies.

Subsequent fusions employing OMB-37 used fetal calf serum (FCS) as a growth supplement, as outlined in Example 5. Rabbit serum was found to complicate the hybridoma identification process since antibodies present in the rabbit serum reduced the specificity of the assay.

SCREENING AND SELECTING ANTIGEN-SPECIFIC CLONES

Once fusions are complete, the wells containing antibody producing cells are grown for approximately 2–3 weeks and positive clones are selected and subcloned for further analysis. Methods for selecting a particular clone of interest are well known in the art of hybridoma technology. For a review of strategies and selection techniques see generally Nakamura, et al., *Immunochemical Assays and Biosensor Technology for the 1990s*. American Society for Microbiology, 1992. Washington D.C. As described in Example 5, the hybridoma supernatants were screened for specific antibody production after day 18. The wells containing hybrids went through three levels of testing designed for this particular antigen. It is contemplated that those with skill in the art of assay development will similarly be able to develop suitable assays for a variety of antigens. Select clones that were positive in each of the three stages of testing, were carried in culture continuously and subcloned at least once to ensure their monoclonality.

Clones expressing GAS specific antibodies were detected using a series of three successive tests. These ELISA formats were developed to detect the presence of Group A Streptococcus specific antibodies in polyclonal sera, hybridoma supernatants, and ascites fluid. All three of the assays are detailed in Example 6. The first test detected the presence of antibodies to the pepsin-digested Group A Streptococcus. The results of the first screen are provided in Table 1 below. In the second screen, antibodies produced from clones passing the first test were retested using two forms of antigen. Pepsin-digested bacterial extracts were used, as in the first screen, and in addition the antibodies were tested using a nitrous acid extract (NAE) of Group A Streptococcus. Methods for preparing nitrous acid extracts of Group A Streptococcus are provided in Example 6. The nitrous acid extract is an enrichment of cell-derived carbohydrate that includes the epitope conferring group-specificity and is presumptive evidence that positive clones are producing antibodies specific for Group A Streptococcus. Positive wells were expanded and were confirmed to be group specific by inhibition with N-acetyl-D-glucosamine which is the epitope recognized by antibodies specific to Group A Streptococcus. Screening is preferably performed over a period of weeks and this is an initial indicator of clone stability. In the third test, antibodies obtained from the positive clones identified in the second test were further tested in an inhibition assay with N-acetyl-glucosamine to ensure that antibody specificity was directed to the GAS carbohydrate epitope. The results from one fusion identified as SA1G are provided in Table 1 below.

As an alternative to these ELISAs, the samples could additionally be tested using a sandwich ELISA coating the rabbit monoclonal antibodies of interest, followed by the antigen and subsequently followed by antigen-specific monoclonal antibodies containing a suitable label to facilitate quantitation.

TABLE 1

| FUSION SUMMARY | | | |
|---|---|---|---|
| | Initial Screen | Retest | Final |
| Antigen | Pepsin | Pepsin & NAE | Inhibition (by N-acetyl-D glucosamine) |
| Purpose | Detection | Confirmation | Specificity |
| Result (SA1G) | 122/2844 (4%) | 30/122 (25%) | 9/30 (30%) |

ASSESSING CLONAL STABILITY

In order for a rabbit monoclonal antibody producing cell line to be useful, it must be stable. Often the products of xenogeneic fusions are unstable. For fusion SA1G, performed using OMB and FCS, as outlined in Example 5, one clone of the nine, identified from the screening tests outlined in Example 6 and in Table 1, column 3 was identified as SA1G7-516. This clone was chosen for subcloning. Subcloning is important for the development of commercializable antibodies because successful subcloning ensures that the clone is stable and homogenous. Therefore, it is contemplated that most antigen-specific rabbit-antibody producing clones identified using the methods of this invention will be subcloned.

As an example of a subcloning strategy, Clone SA1G7-516 was subcloned by limiting dilution (⅓ cell/well) 4 months after fusion. Cells were distributed into 6, 96-well plates and 55 subclones were screened for antibody specificity. From these 55 subclones, 15 were positive (27%). It is anticipated that other clones will generate different percentages of subclone positivity. It is expected that xenogeneic fusions will likely have a somewhat reduced rate of subclone positivity as compared with allogeneic or syngeneic fusions involving murine×murine or rat×rat.

These clones were followed for long term stability. Stability is preferred for consistent commercial assay development. One subclone, SA1G7-516.5 was followed for long term stability with periodic testing for reactivity on pepsin-digested Group A Streptococcus (See Example 6 for methods). This clone as well as others generated by this method was stable for over 12 months in culture and continues to produce GAS specific antibodies.

Figure 3:
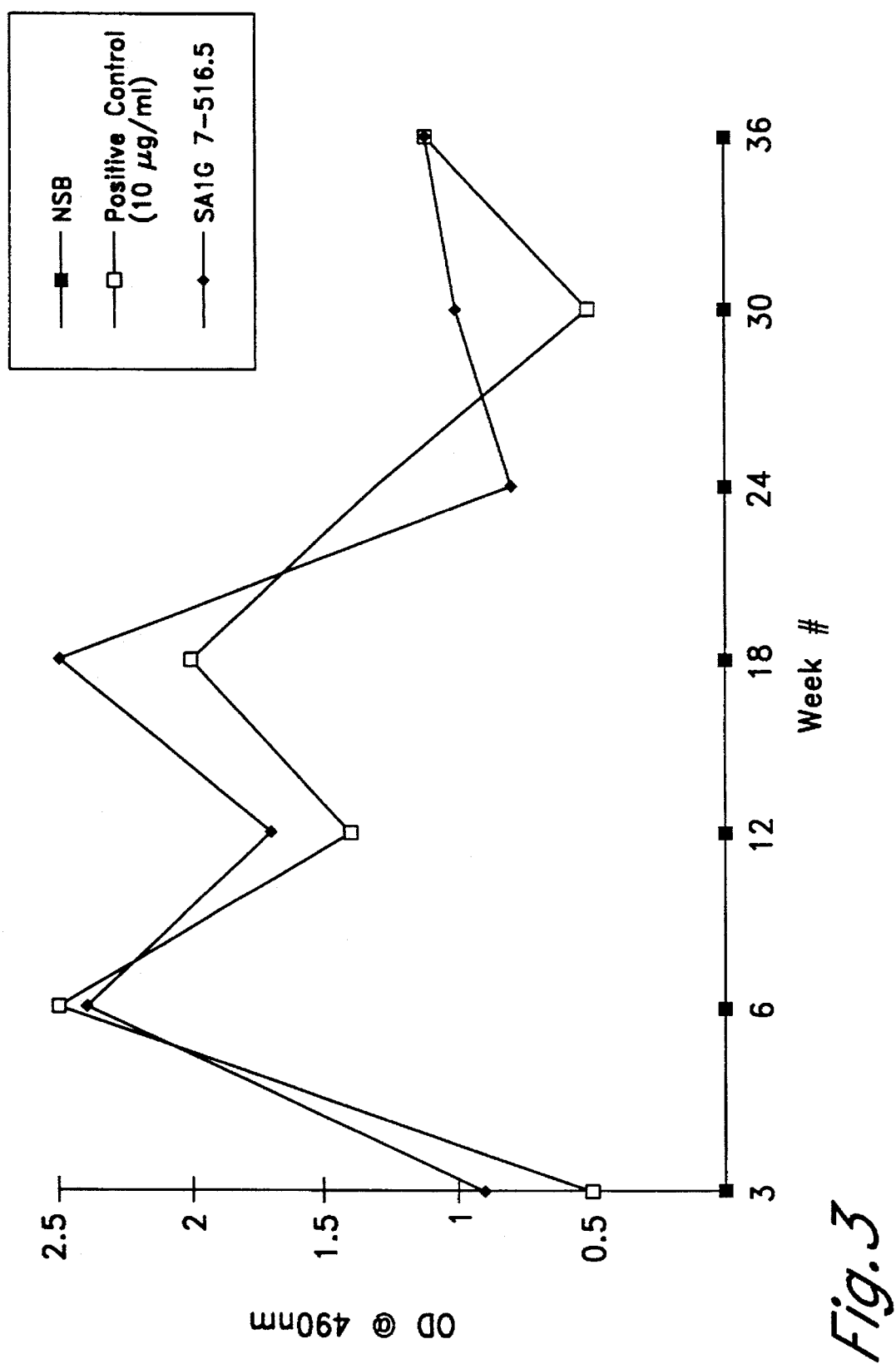
FIG. 3 diagrams the results of ELISAs to determine the stability of the heterohybrid SA1G7-516.5 as compared with a commercially prepared rabbit anti-Group A Streptococcus polyclonal antibodies at a concentration of 10 μg/ml. NSB (non-specific binding) indicates background due to non-specific adherence of the antibodies in tissue culture supernatants.

FIG. 3 illustrates the stability of the clone SA1G7-516.5 as compared with a positive control. The positive control is commercially available rabbit polyclonal anti-Group A Streptococcus serum diluted to a constant concentration for each testing date. The positive control serves as a measure of assay consistency. The clone SA1G7-516.5 was kept in culture for nine months and periodically tested for rabbit IgG secretion in an antigen specific assay such as one of those described in Example 6. Pepsin-digested Group A Streptococcus was coated onto a plate. Culture supernatant was detected using goat anti-rabbit IgG horseradish peroxidase conjugate using ortho-phenylamine diamine (OPD, Sigma, St. Louis, Mo.) as a substrate. Results provided in FIG. 3 were read from an ELISA plate reader at $OD_{490}$. Increasing optical density corresponds to increasing quantity of antibodies. FIG. 3 indicates that as compared with the positive control, the clone SA1G is stable over time.

As an additional measure of the usefulness of the method for generating rabbit monoclonal antibodies as compared with other methods available in the art, a comparison was made of the stability and antibody output of an exemplary clone prepared and deposited by Raybould, et al. as a fetal calf serum adapted cell, ATCC HB 9696. The experimental details are provided in Example 7. HB 9696 was grown in Dulbecco's Minimum Essential Medium (DMEM) with 10% fetal calf as directed by Raybould. Table 2 provides a comparison of clones derived from the methods of this invention as compared with ATCC clone HB 9696. The results of Table 2 were generated using an antigen-specific ELISA of either NAE or pepsin-digested Group A Streptococcus. Rabbit Group A Streptococcus polyclonal antibodies and rabbit monoclonal antibody derived from clones SA1F 7-205, 7-479, 7-490 and 7-572 were compared to antibody from HB 9696 as well. Like SA1G clones, the SA1F clones were derived from the fusion of rabbit splenocytes with OMB-037 using methods identical to those disclosed for SA1G (see Example 5).

Table 3 provides the results of assays to quantitate the amount of rabbit immunoglobulin produced by the cultures. Group A Streptococcus polyclonal antibodies ranging from 1.6–1000 ng/ml was used to determine the IgG concentration by ELISA. ATCC HB 9696 failed to produce detectable antibodies using the growth conditions provided by ATCC as compared to the SA1G clones that had similarly been frozen and thawed at least once.

TABLE 2

| EVALUATION OF RMH-B52 Ag specific assay | | |
|---|---|---|
| | NAE (OD @ 490 nm) | Pep (OD @ 490 nm) |
| NSB | 0.0 | 0.0 |
| Positive (10 µg/ml) | 3.9 ± 0.05 | 2.9 ± 0.1 |
| Negative | 0.0 | 0.0 |
| Our clones: | | |
| SA1F 7-205 | 2.9 | 0.7 |
| SA1F 7-479 | 2.6 | 1.2 |
| SA1F 7-490 | 2.8 | 0.7 |
| SA1F 7-572 | 2.6 | 1.2 |
| ATCC clone: | | |

TABLE 2-continued

| EVALUATION OF RMH-B52 Ag specific assay | | |
|---|---|---|
| | NAE (OD @ 490 nm) | Pep (OD @ 490 nm) |
| RMH-B52 | 0.0 ± 0.0 | 0.0 ± 0.0 |

TABLE 3

| Rabbit Immunoglobulin Assay | | |
|---|---|---|
| | Standard | OD @ 490 nm |
| Positive | 1000 ng/ml | 3.1 ± 0.23 |
| | 200 ng/ml | 2.9 ± 0.26 |
| | 40 ng/ml | 1.4 ± 0.04 |
| | 8 ng/ml | 0.4 ± 0.0 |
| | 1.6 ng/ml | 0.1 ± 0.0 |
| Negative | 0 ng/ml | 0.0 ± 0.0 |
| RMH-B52 | Culture sup | 0.0 ± 0.0 |

PRODUCTION AND PURIFICATION OF RABBIT MONOCLONAL ANTIBODIES

Antibodies can be produced in quantity in vitro or in vivo. However, in vivo production of antibodies as ascites generates higher concentrations of antibodies more quickly than in vitro expansion. Most xenogeneic fusions do not grow well in ascites in part because the mouse hosting ascites growth recognizes the fusion product as foreign. Determinants expressed on the surface of the clones are similarly seen as foreign, hence the efficiency of ascites production is compromised by humoral and cellular immune responses.

To circumvent the immune responses associated with xenogeneic antibody production, the clones were grown as ascites in either nude or severe combined immunodeficient mice (SCID). Techniques for handling immunodeficient mice are known in the art, therefore these precautions will not be reiterated here.

Stable hybridoma clones from xenogeneic fusion partners are preferably injected into nude or severe combined immunodeficient mice (see Example 8). Methods for ascites production are also well known in the art (see Harlow, et al. supra.). Briefly, the clones were prepared in growth media (HB-GRO with 10% FCS) and injected into the nude or SCID mice that were primed with incomplete freunds adjuvant five days before receiving the clones.

Figure 4:
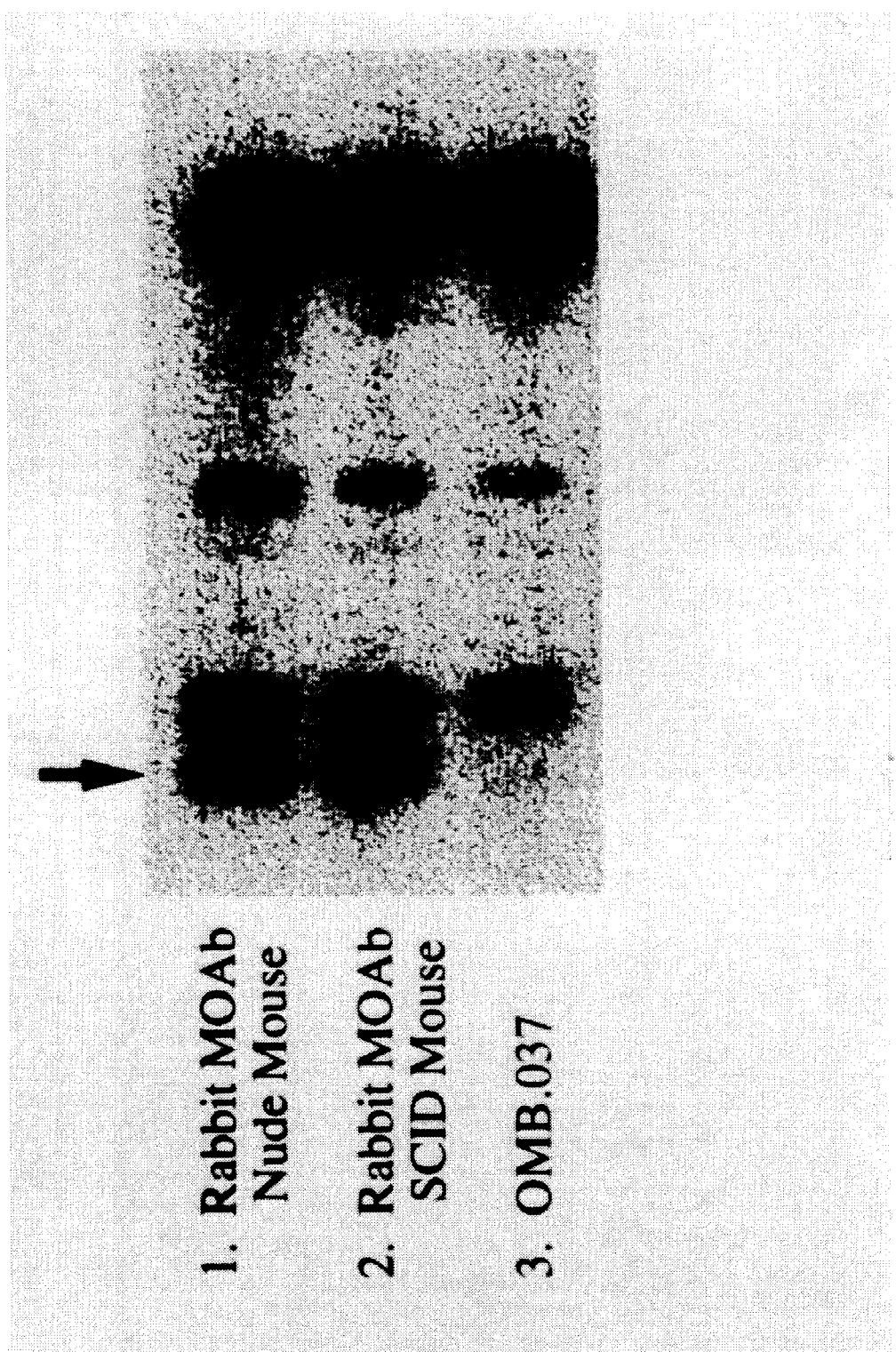
FIG. 4 is a photograph of a cellulose acetate gel containing aliquots of crude ascites. Lanes 1 and 2 contain aliquots of crude ascites from heterohybridoma SA1G7-516.5. Lane 3 is from fusion partner OMB-037.

Samples of ascites were tested for the presence of rabbit-derived and mouse-derived antibodies and for antibody specificity to the particular antigen of interest. Two to three weeks after injection of the clones into the mice, the peritoneal ascites fluid was collected and a sample was loaded onto a cellulose acetate gel to check for the presence of antibody protein. Cellulose acetate gel electrophoresis separates molecules based on charge. FIG. 4 is a photograph of a cellulose acetate gel containing aliquots of crude ascites using clone SA1G7-516.5. The photograph indicates that the SA1G cells produce antibodies as ascites in both nude and SCID mice. The arrow indicates the presence of immunoglobulin in the rabbit samples from both nude and SCID mice. Moving to the right, the next band is transferrin and the heavy band on the far right of the photograph is albumin. The ascites derived from the clones was additionally tested by ELISA using the methods of Example 6 to confirm the specificity of the rabbit antibodies against Group A Streptococcus.

The antibody content and the presence of rabbit monoclonal antibodies in the ascites was confirmed using the three assays described in Example 6. In the first assay, pepsin-digested GAS (at a concentration of 1:400 of 1 OD=$A_{660}$) was coated onto a plate. The ascites was added and probed with goat anti-rabbit antibodies conjugated to horseradish peroxidase (HRP) (Fischer Biotech Pittsburgh, Pa. using 0.4 mg/ml stock diluted 1:1000). The titration of ascites in both nude and SCID mice was compared with ascites production using OMB-037 as a control. The results indicated that the SA1G preparations contained large amounts of rabbit antibodies. Results of this assay are provided in FIG. 5.

The presence of contaminating murine immunoglobulin and the usefulness of SCID mice as ascites hosts as compared with nude mice was determined using an assay for mouse immunoglobulin. This ELISA used a goat anti-murine IgG (Fischer Biotech, Pittsburgh, Pa., at 1 mg/ml, 250 ng/well) as a coating antibody. Ascites samples were added and mouse-derived antibodies were detected using a second goat anti-murine antibody labelled with HRP (Fischer Biotech, 0.4 mg/ml, 20 ng/well). Results are provided in FIG. 6. Samples OMB-037 and SA1G, both from nude mice, contained large amounts of murine immunoglobulin. Conversely, the SA1G ascites obtained from SCID mice contained very little murine immunoglobulin.

Ascites from hybrids of a murine×murine fusion contain antibodies from both the hybrid cell and from the host producing the ascites. This is true when xenogeneic hybrids are injected as well and these mouse antibodies could pose a problem in purification since murine antibodies would be purified together with rabbit antibodies. The use of SCID mice, having a blockage of both T and B cell maturation, is shown (see FIG. 7) to reduce the background of murine immunoglobulin. Thus, it is contemplated within the scope of this invention that rabbit monoclonal antibodies generated by the methods of this invention, are advantageously grown as ascites, preferably in SCID mice, to obtain commercial quantity and quality of antibodies.

The specificity of the rabbit antibodies produced by ascites was determined by a capture assay for antigen-specific immunoglobulin. Pepsin-digested group A Streptococcus or NAE extracted carbohydrate was used to coat the ELISA plates. Aliquots of ascites were added and the reactive antibodies were detected with goat anti-rabbit IgG labelled with HRP. Results of these comparisons are provided in FIG. 7. While ascites using the OMB-037 clone failed to react to the specific antigen, SA1G clones grown in either the nude or SCID mice produced antigen specific antibodies.

PURIFICATION OF RABBIT MONOCLONAL ANTIBODIES FROM ASCITES

Purified monoclonal antibodies are required for consistent reactivity in diagnostic assays. Contaminating protein, including immunoglobulin, decreases the level of sensitivity in immunoassays by increasing non-specific reactivity. For many applications, column purification is not always necessary, however for the repeatable and consistent performance of monoclonal antibodies, purification is generally required. There are a variety of methods known to those with skill in the art for antibody purification and therefore, the proposed methods for antibody purification outlined below should not be construed as limiting upon the scope of the invention.

The ascites fluid containing antibodies was clarified with saturated ammonium sulfate and lipoprotein was removed by dextran sulfate precipitation. Rabbit antibodies were purified by separation on Q SEPHAROSE (an agarose matrix) columns (Pharmacia, Piscataway, N.J.) or on N-acetyl-glucosamine agarose immunoaffinity columns. Procedures for separating and purifying antibodies using column chromatography are known in the art. Basic methods in column chromatography that can be adapted to accommodate the rabbit monoclonal antibody purification include those of Clezardin, et al. and Tasaka, et al. (J. Chromatogr. 319:67–77 1985 and Acta Hitochem. Cytochem 17:283–286, 1984 respectively, which are hereby incorporated by reference). The various fractions were eluted from the column and tested by ELISA. The single peak containing rabbit immunoglobulin was tested using methods described in association with FIG. 5 and the Group A anti-streptococcus activity was confirmed using methods described in association with FIG. 7. An exemplary methodology for rabbit monoclonal antibody purification is provided in Example 9.

The $K_a$ of the antibodies was determined using techniques well known in the art (see Lindmo, et al., J. Immunol. Methods 72:77–89, 1984) Briefly the Ka was determined using a solid phase assay by immobilizing the antigen, here the NAE extract, onto polystyrene beads precoated with rabbit polyclonal anti-GAS antibodies (Immucell, Portland, Me.). Procedures for conjugating antibodies to polystyrene beads are available from manufacturers and are well known in the art. The polyclonal antibodies were saturated with NAE obtained from the Group A Streptococcus. $I^{125}$-labelled and unlabelled SA1G monoclonal antibodies were titrated against a constant amount of antigen conjugated to the bead. The $K_a$ was calculated using Scatchard analysis. In this example, antibodies produced from clone SA1G7-516.5 was determined to be $2.74\pm0.64\times10^9$. The $K_a$ plot is provided in FIG. 7.

Rabbit monoclonal antibodies produced using the methods of this invention can be used as substitute antibodies for murine polyclonal or monoclonal antibodies or for rabbit polyclonal antibodies or employed for any number of uses known in the art of immunology. Therefore, the rabbit monoclonal antibodies produced by the methods of this invention can be used in fluorescent assays, as capture molecules for the purification of antigen, and in diagnostic assays such as Western blot, radioimmunoassays, enzyme-linked immunosorbent assays and in immunochromatographic assays. For an example of the use of the rabbit monoclonal antibodies of this invention in applications suited for diagnostic assay development, see the assays disclosed in Example 6.

Other devices or one-step immunoassays that can incorporate the rabbit monoclonal antibodies of this invention include the CONCISE® device (an immunoassay device) (Hybritech, LaJolla), the TESTPACK® device (an immunoassay device) of Abbott Laboratories (North Chicago, Ill.), described in European Patent Application No. 217,403, published Apr. 8, 1987 or similar test devices. Still other devices containing porous membranes that can be adapted to employ the rabbit monoclonal antibodies of the present invention include the devices of Bauer, et al., U.S. Pat. Nos. 3,811,840, issued May 21, 1974; Brown, III, et al., 4,916, 056, issued Apr. 10, 1990; Cole, et al., 4,407,943, issued Oct. 4, 1983; Cole, eg al., 4,246,339, issued Jan. 20, 1981; Intengan, 4,440,301, issued Apr. 3, 1984; Jolley, 4,704,255, issued Nov. 3, 1987; Katz, et al., 4,496,654, issued Jan. 29, 1985; and Tom, et al., 4,366,241, issued Dec. 28, 1982, all of which are incorporated herein by reference.

The rabbit monoclonal antibodies of the present invention can be used in chromatographic methods such as, for example, those described in Weng, et al., U.S. Pat. No. 4,740,468, issued Apr. 26, 1988, incorporated herein by reference, and published European Application No. 186,100 to Yue, et al., published Jul. 2, 1986.

Those with skill in the art of assay development will be readily able to make the appropriate modifications to these assays to use rabbit monoclonal antibodies directed to other antigen or antibodies. The rabbit monoclonal antibodies can be used in therapeutic applications as targeting molecules for therapeutic modalities and for imaging reagents.

In a particularly useful application of the rabbit monoclonal antibodies of this invention, it is contemplated that the antibodies can be used in solid-phase immunoassay devices. Such devices include the non-chromatographic ICON® and like devices described in Valkirs, et al., U.S. Pat. Nos. 4,632,901 and 4,727,019, issued Dec. 20, 1986 and Feb. 23, 1988, respectively, herein incorporated by reference. ICON® is a trademark of Hybritech Incorporated (San Diego, Calif.) for the devices described in the Valkirs, et al. In these assays, a first antibody or antigen is bound or fixed to a porous member such as a porous membrane, filter or the like. A porous membrane may be comprised of a flexible or rigid matrix made from any of a variety of filtration or chromatographic materials including glass fibers, microfibers, and natural or synthetic materials. Fluids should be able to flow into and pass easily through the porous membrane. The membrane should also preferably have pore sizes of at least 0.1 μ and preferably no more than 20 μ. The porous membrane can be used alone or as part of a more elaborate device.

The test sample fluid, applied to the porous member, flows through the member and contacts the antibodies or antigen thereon. A test analyte present in the test sample fluid is bound by the first antibody on the porous member.

Following the application of sample fluid, a second solution is added that preferably contains a solution of antibodies. This second antibody preferably binds the test analyte at an epitope that does not interfere with the binding of the first antibody or antigen. In another preferred embodiment, the test sample is first processed to facilitate analyte detection and mixed with the second antibody before the test sample is applied to the porous member. The antibodies present in the detecting antibody solution is preferably labelled with a detection tag such as an enzyme for colormetric analysis, radionucleotide, fluorescent label, colored latex particles or the like. Additional steps are added, if necessary, to visualize the labelled tag bound to the test analyte on the porous member. The presence of the analyte in the sample fluid is detected as a positive signal on the surface of the porous member.

Applications of such assays in the art are well known and are detailed in publications by Anderson, et al. and by Valkirs (Clin. Chem. 32(9):1692–1695, 1986; Laboratory Medicine 19:564–567, 1988 respectively, both publications are hereby incorporated by reference). In Example 10, the rabbit monoclonal antibodies of this invention recognize Group A Streptococcus-specific antigen. It is anticipated that these assays, employing rabbit monoclonal antibodies, will be developed for any number of antigen or antibody detecting schemes including assays to detect human choriogonadotropin (HCG), lutropin (LH), or antibodies directed to HIV-1 or the like.

Solid-phase immunoassays are available in a number of different configurations. In a preferred configuration, the assay format follows the format of Anderson et al. and like Anderson et al., includes an internal reference. This assay format employs the rabbit monoclonal antibodies of this invention in the ICON® assay methodology for solid-phase immunoassays as either a first antibody (the capture antibody) or as a detecting antibody. In another preferred embodiment, both antibodies employed for capturing and detecting antigen in a solid-phase immunoassay are rabbit monoclonal antibodies.

Example 10 details the use of the ICON® methodology for the identification of Group A Streptococcus infection.

Table 4 illustrates the results of an ICON® format assay for Group A Streptococcus using rabbit monoclonal antibodies for both the capture and detecting antibodies. Bacteria and yeast samples were processed as disclosed in Example 10, using methods similar to those employed if the bacteria were isolated from a throat swab. The bacteria were applied as test sample fluid to the porous membrane. The ± designation in Table 4 indicates the presence or absence of rabbit monoclonal antibody reactivity to the organisms listed in the left column. The results indicated that the rabbit monoclonal antibodies are Group A Streptococcus specific. It is recognized in the art that some preparations of antibodies directed to Group A Streptococcus antigen N-acetyl glucosamine may also bind to antigenic determinants present on *Staphylococcus aureus*. Since *S. aureus* may be present in sample fluid, such as a resuspended throat swab, assays to detect Group A Streptococcus will have some level of false positives if the antibodies employed in the assay additionally recognize *S. aureus*. Results obtained from assays using antibodies that additionally recognizes *S. aureus* extracts should be confirmed by another method. Advantageously, the rabbit monoclonal antibodies of this invention, did not bind to *S. aureus* which, as noted above, is traditionally a concern in Group A Streptococcus immunoassays. Thus, the use of rabbit monoclonal antibodies of this invention, generated to Group A Streptococcus obviates the need for confirming positive results by a second test method.

TABLE 4

STREPTOCOCCUS A SOLID PHASE IMMUNOASSAY (MONO/MONO) SPECIFICITY TESTING

| | | |
|---|---|---|
| 1. Streptococcus Group D | CDC SS754 | – |
| 2. Streptococcus Group A | Non-Beta (clin isolate) | + |
| 3. *Staphylococcus saprophytilus* | ATCC 15305 | – |
| 4. Streptococcus Group B II | SS 619 | – |
| 5. *Escherichia coli* | ATCC 25922 | – |
| 6. Streptococcus Group D | ATCC 19434 | – |
| 7. Streptococcus Group G | SS868 | – |
| S. Streptococcus Group C | SS188 | – |
| 9. Streptococcus Group B Ib | SS618 | – |
| 10. Streptococcus Group B | SS700 | – |
| 11. Streptococcus Group A | ATCC 19615 | + |
| 12. Streptococcus Group B III | SS462 | – |
| 13. Staphylococcus Group A | Cowan I CDC | – |
| 14. *Klebsiella pneumonias* | ATC 23357 | – |
| 15. Streptococcus Group C | SS189 | – |
| 16. *Candida albicans* | HMCC 063 | – |
| 17. Streptococcus Group A | SS721 | + |
| 18. Streptococcus Group A | SS410 | + |
| 19. Streptococcus Group B Ia | SS615 | – |

Figure 9:
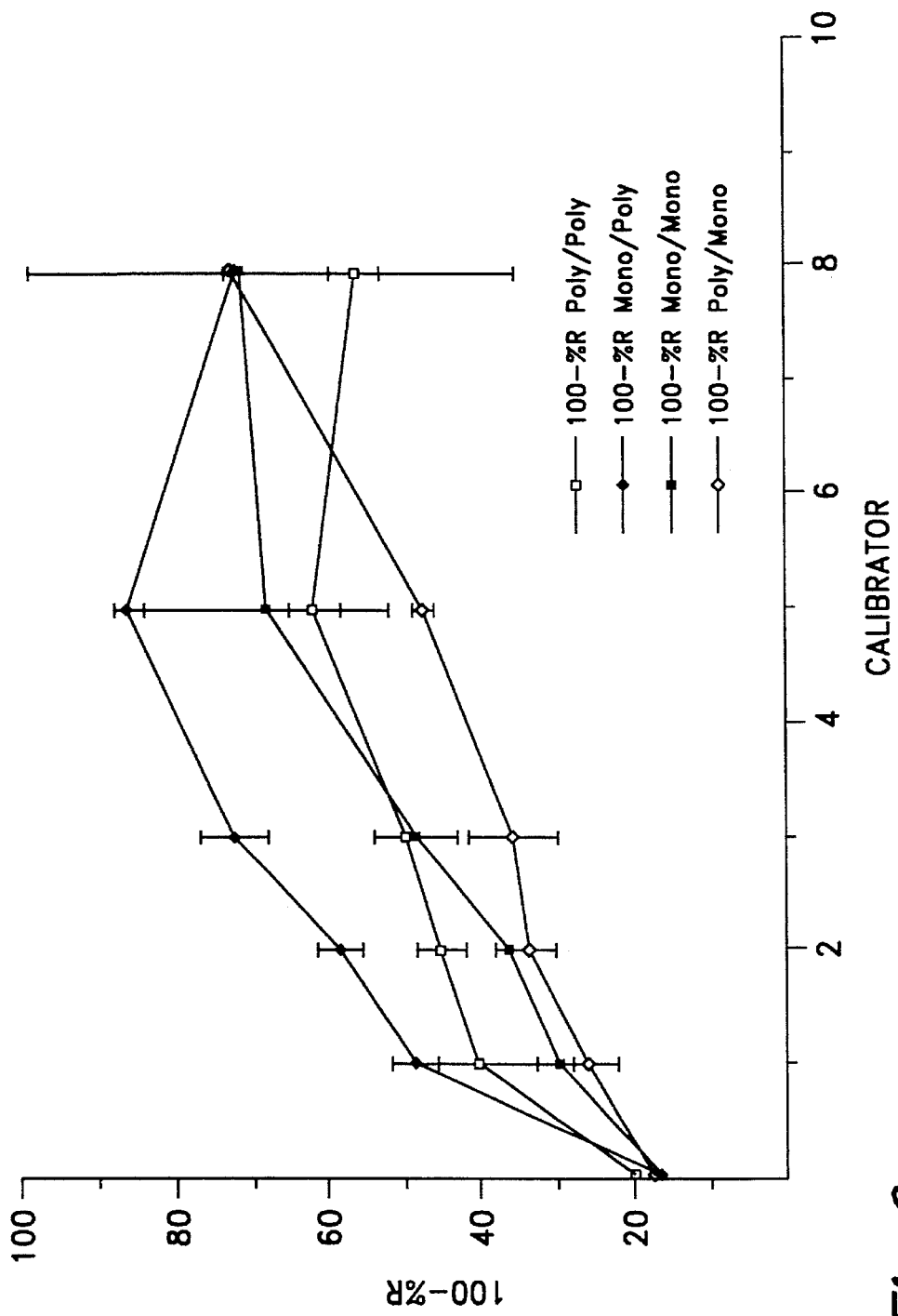
FIG. 9 compares the reflectance of different concentrations of bacterial lysate using four different combinations of monoclonal or polyclonal rabbit antibody preparations.

Current assays for Group A Streptococcus use rabbit polyclonal antibodies for both the detecting antibody and the capture antibody. FIG. 9 illustrates the results of a study to compare different rabbit antibody format assays. Group A Streptococcus was diluted from $2 \times 10^8$ colony forming units (CFU)/ml to $1.56 \times 10^6$ CFU/ml as provided below in Table 5. Twenty microliters of this suspension was processed in the ICON® format assay (See Example 10 or commercially available from Hybritech, Incorporated, San Diego, Calif.) using various combinations of rabbit monoclonal and rabbit polyclonal antibodies as detecting or capture antibodies. These particular four ICON® format assays were prepare using rabbit polyclonal antibodies as detector antibodies with rabbit polyclonal antibodies as capture antibodies (poly/poly), rabbit monoclonal antibodies as detector antibodies with rabbit polyclonal antibodies as capture antibodies (mono/poly), rabbit monoclonal antibodies as detector antibodies with rabbit monoclonal antibodies as capture antibodies (mono/mono) and rabbit polyclonal antibodies as detector antibodies with rabbit monoclonal antibodies as capture antibodies (poly/mono).

Increasing numerical values on the Calibrator scale in FIG. 9 corresponds to increasing bacterial concentrations. The reflectance (R) of the signal on the immunoassay was determined using a Model 1500 Plus reflectometer (Macbeth, Newburgh, N.Y.) and data was expressed as 100-% R. The results indicated that all combinations of capture and detecting antibodies are well suited for solid-phase immunoassays. Therefore, rabbit monoclonal antibodies, produced by the methods of this invention, can replace rabbit polyclonal antibodies in a Group A Streptococcus solid-phase immunoassay. It is contemplated that those with skill in the art of immunoassay development will similarly be able to make comparisons between rabbit polyclonal and rabbit monoclonal antibodies and between rabbit monoclonal and mouse monoclonal antibodies and select the desired antibody population based on its effectiveness and convenience in a particular assay.

TABLE 5

ICON ® Format Assay Comparing
Rabbit Polyclonal and Rabbit Monoclonal Antibodies

| Calibrator Number | Bacteria concentration CFU/ml | Bacterial Concentration CFU/Assay |
|---|---|---|
| 1 | $1.56 \times 10^6$ | $3.12 \times 10^4$ |
| 2 | $3.13 \times 10^6$ | $6.26 \times 10^4$ |
| 3 | $6.25 \times 10^6$ | $1.25 \times 10^5$ |
| 5 | $2.50 \times 10^7$ | $5.00 \times 10^5$ |
| 8 | $2.00 \times 10^8$ | $4.00 \times 10^6$ |

Particular embodiments of the invention are discussed in detail and reference has been made to possible variations within the scope of this invention. There are a variety of alternative techniques and procedures available to those of skill in the art which would similarly permit one to successfully perform the intended invention.

EXAMPLE 1

Generation of Fusion Partner OMB-037

To generate the fusion partner, a rabbit was immunized with bovine somatotropin (BST) using the following immunization protocol. Three days prior to fusion, the rabbit was given a 50 µg I.V. boost of BST. One day prior to the fusion, mouse murine-derived macrophage feeder cells were collected and plated at 10,000 cells/well in 10% fetal calf serum (GIBCO, heat inactivated 56°C., 30, mn) plus 1×HAT. The spleen yielded $300 \times 10^6$ cells. The cells were divided in half and 2 separate fusions were performed. A 5:1 ratio of spleen cells to SP2/0 cells was fused in 43% PEG. The cells were plated at $10^5$ cells per well in 15% Rabbit sera, 1×HAT on top of the feeder cells. Two weeks post fusion, the media was removed and replaced with 10% FCS, 1×HT. Fusion #1 had approx. 10% wells with growth and fusion #2 had approx. 50% wells with growth. The plates were screened in an ELISA using wells coated with 250 ng/well BST in carbonate buffer. All were negative for anti-BST Ab. The cells were grown in 20 µg/ml 8-azaguanine to find a HAT sensitive mutant (method provided in Example 3). One HAT sensitive line was tested for the presence of rabbit IgG by capture assay as described in Example 6. No Ab was detected down to 80 ng IgG/ml supernatant. At this point the cells were frozen using the methods described in Example 2.

EXAMPLE 2

Long Term Storage and Use of Fusion Partner

Cells grown in log phase were centrifuged (300× g, 10 minutes) and resuspended in freezing medium (MEM+30% horse serum +10% DMSO). Cells were frozen at a cell concentration of $5 \times 10^6$ cells/1 ml. vial (NUNC, Vangard International, N.J.). Cells were frozen in a controlled rate freezing chamber (1 degree/min) (Cryomed, Inc., New Baltimore, Mich.) and were stored in liquid nitrogen.

Vials were thawed from liquid nitrogen storage in a 37° C. water bath. Cells were diluted with 1 ml of HB-GRO medium (Irvine Scientific, Santa Ana, Calif.) and 10% horse serum and transferred to a 15 ml conical tube containing 10 ml of HB-GRO+10% HS. Cells were centrifuged and plated at $2 \times 10^5$ cells/ml for culturing.

EXAMPLE 3

Establishing 8-azaguanine Resistance and HAT Sensitivity $1.2 \times 10^7$ cells grown in log phase were centrifuged (300× g, 10 minutes) and resuspended in 12 ml of HB-GRO+10% horse serum supplemented with 20 µg/ml of 8-Azaguanine (Calbiochem, La Jolla, Calif.). The cells were plated in 24 well plates at 2 ml/well. The cells were fed with HB-GRO media supplemented with 8-azaguanine every 3 days until colonies appeared. The colonies were grown to confluence and split into two portions. This was repeated for 5 cycles. The media was replaced in ½ of the wells with medium containing HAT (Sigma, For 100×: Hypoxanthine 10 mM, Aminopterine 0.04 mM, Thymidine 1.6 mM). Cell death indicated HAT sensitivity and the corresponding wells not exposed to HAT were expanded for fusion.

EXAMPLE 4

Exemplary Immunization Protocol for Rabbit Monoclonal Antibodies Directed to Carbohydrate The following immunization protocol was used to immunize New Zealand white rabbits (Siminek, Vista, Calif.) with pepsin-digested Group A Streptococcus variant A486.

Pepsin-digested *Streptococcus pyogens* (ATCC 19615) was prepared by growing the cells in Todd-Hewitt Broth at 37° C. The cells were heat killed at 70° C. for 1.5 hours. The bacteria were resuspended in 1 mg/ml pepsin at pH 2.8 in 0.85% NaCl and incubated for 2 hours at 37° C. The cell digest was washed 3 times with PBS (Phosphate Buffered Saline). The digest was diluted to $A_{660}$=0.38–0.40.

The immunization protocol is provided below:

| Day: | | | |
|---|---|---|---|
| 1 | 3 | 5 | 0.5 ml/day IV |
| 8 | 9 | 11 | 1.00 ml/day IV |
| 12 | 15 | 16 | 1.00 ml/day IV |
| 18 | 19 | 29 | 1.00 ml/day IV |

Rabbits were bled on day 22 and spleens were removed on day 32. The rabbit serum was tested by ELISA using pepsin-digested digested Group A *Streptococcus pyogens* (GAS) as described in Example 6.

EXAMPLE 5

Fusion of Rabbit Antibody Producing Cells with Exemplary Fusion Partner OMB-037

A single cell suspension of rabbit splenocytes was obtained from a rabbit immunized with Group A Streptococcus using the immunization protocol provided in Example 4. The splenocyte cell concentration was adjusted to $2.5 \times 10^6$/ml in PBS. Leu-leu-ome peptide was added at 250 μM/1 to kill the lysosomal-enriched cells such as macrophages. The mixture was incubated for 15 minutes at room temp. The cells were spun down and the pellet was mixed with the fusion partner OMB-037 at a ratio of 4 spleen cells per OMB-037. The fusion was accomplished by slowly adding 1 ml of 35% PEG 1500 (Aldrich, Milwaukee, Wis.) to the cell pellet/OMB-037 mixture for one and half minutes and gradually diluted with serum free media followed by serum containing medium. The fusion mixture was brought up to a cell density of $8 \times 10^5$ cells/ml in 150 mls. in HB-GRO containing 15% fetal calf serum and HAT, as disclosed in Example 3, and distributed into 96 well plates at $2.0 \times 10^5$ cells/well. The cells were incubated at 37° C. in an atmosphere containing 5–10% $CO_2$.

After fusion, the cultures were examined for hybridoma growth. The presence of larger cells and evidence of cell replication were the primary criteria used to assess hybridoma growth. The cells were fed with HAT containing medium on days 5, 8, and 13. The hybridoma supernatants were screened for specific antibody production after day 18. The product of one fusion experiment, used in subsequent analysis is designated SA1G.

EXAMPLE 6

Testing Fusions for Antibody Production

Three tests were used to assess rabbit monoclonal antibody production directed to Group A Streptococcus (GAS)

1) ELISA for Group A Streptococcus (GAS) antibodies: Two forms of antigen were used to test for the presence of specific antibodies. The first preparation employed pepsin-digested *Streptococcus pyogenes* cells. A method for preparing pepsin-digested cells is provided in Example 2. Nitrous acid extract preparations of Group A Streptococcus carbohydrates were obtained by incubating *Streptococcus pyogenes* in 1M HCL and 6M $NaNO_2$. 1M potassium Phosphate was used to stop the reaction. The lysate was centrifuged and the supernatant collected and filtered through a 0.2 μm filter, concentrated and dialyzed against PBS. The nitrous acid extract (NAE) was diluted to a concentration of 1.6 mg/ml.

Either the pepsin digest preparation or the nitrous acid extract was used to coat the wells of Falcon 96 well assay plates. To coat the plates, 50 μl of antigen of a 1:400 dilution of stock pepsin-digested GAS or stock NAE in carbonate buffer pH 9.5 was added to each well. The plates were incubated at 37° C. overnight. Free absorption sites were saturated with 2% bovine serum albumin (BSA) in phosphate buffered saline containing 0.1% Tween (PBS/Tween). Fifty μl of each test sample was added to the plate and incubated at 37° C. for an hour. Unbound materials was removed by washing three times with PBS/Tween. Goat anti-rabbit IgG antibodies conjugated to horseradish peroxidase in 50 μl was added and incubated for an additional hour. After washing, 100 μl of the substrate o-phenylenediamine dihydrochloride (OPD) was added and incubated at room temperature for 15 minutes. The presence of antibodies to Streptococcus A was demonstrated by an increase in absorbance at 490 nm.

2) Sandwich ELISA test for IgG: Falcon Probind assay plates were coated with 50 μl per well of goat anti-rabbit IgG in sodium phosphate buffer pH 7.0. Test samples were added and the procedure followed the assay described above. A similar sandwich assay for detecting mouse IgG was also used to confirm the species of antibody production both for cell culture supernatants and ascites. No cross reactivity was found in either of the rabbit and mouse IgG assays.

3) Inhibition ELISA for Group A Streptococcus Antigen: The procedure was the same as Group A Streptococcus assay (#1, above) with the exception that equal volumes of 20% N-acetyl-D-glucosamine and test samples were co-incubated at 37° C. for one hour. The resulting decrease in absorbance at 490 nm indicated the presence of antibodies to the Group A Streptococcus specific carbohydrate epitope.

After three stages of testing, the desired hybridomas were carried in culture continuously and subcloned at least once to ensure the monoclonality. All subcloning was performed by limiting dilution to assure monoclonality using ⅓ cell per well.

EXAMPLE 7

Comparison of Rabbit Monoclonal Antibody Producing Clone HB 9696 with Rabbit Monoclonal Antibody Producing Clone SA1G7.

Nitrous acid extracts of Group A Streptococcus (GAS) (the antigen used to produce clone HB 9696) or pepsin-digested Group A Streptococcus were coated onto ELISA plates. The concentration of NAE product per well was 125 ng. The supernatant from cells grown to confluence in DMEM media supplemented with 10% fetal calf serum was added to the wells. Following a 1 h incubation at 37° C., the plates were washed and bound antibodies were detected with a goat anti-rabbit HRP conjugate. As positive controls, rabbit Group A Streptococcus purified polyclonal antibodies and several clones from the fusion protocol generated with OMB-037 were added. The results are provided in Table 2. HB 9696 did not produce antibodies specific for Group A Streptococcus, nor were the cells stable in culture, even in the presence of rabbit sera.

To determine if HB 9696 was making antibodies, an initial screen quantitative ELISA was prepared in which a standard curve (GAS polyclonal) ranging from 1.6–1000 ng was used to determine the immunoglobulin concentration. The results are provided in Table 3. HB 9696 did not produce detectable antibodies. The clone was either inherently unstable or particularly susceptible to freeze/thaw procedures. Both qualities weigh strongly against the use of these fusion partners and antibody producing cells for the production of commercial quantities of antibodies.

EXAMPLE 8

Growth of Xenogeneic Antibody Producing Clone as Ascites

The stable hybridoma clones were prepared in growth medium, injected into nude or SCID mice (primed with incomplete Freunds adjuvant, 0.5 ml/mouse, five days prior to inoculation), at a concentration of $2 \times 10^6$ cells per mouse. After two to three weeks, peritoneal ascites fluid was collected and quick-checked on cellulose acetate gel for the presence of antibodies. The antibody-containing ascites was further tested using the ELISAs described in Example 6 to detect rabbit antibodies against Group A Streptococcus.

Figure 5:
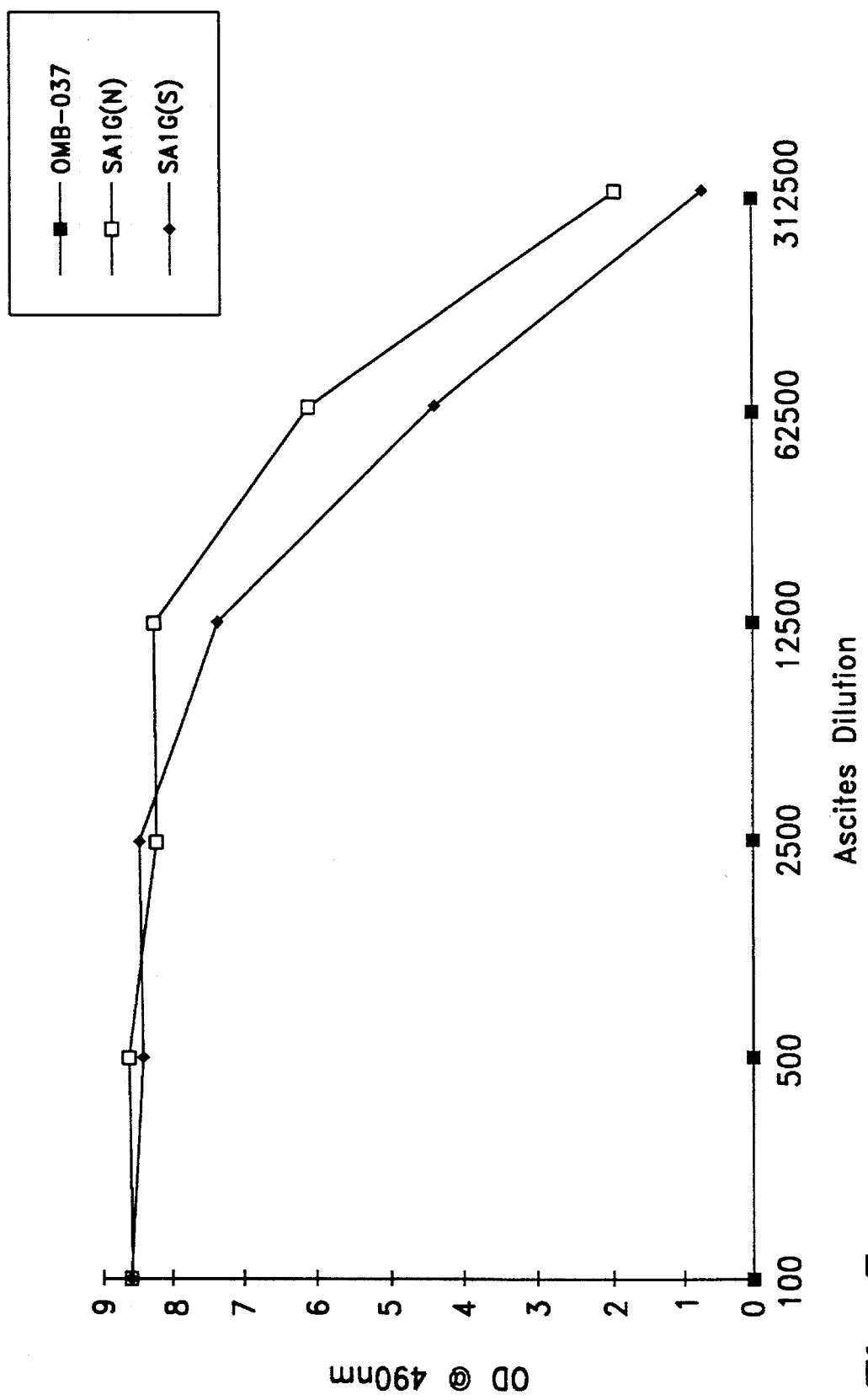
FIG. 5 illustrates the results of an ELISA to test for the presence of rabbit immunoglobulin in ascites fluid obtained from the heterohybridoma SA1G7-516.5 as compared with the fusion partner OMB-037. (N) and (S) denote immunoglobulin produced in nude or SCID mice respectively.
Figure 6:
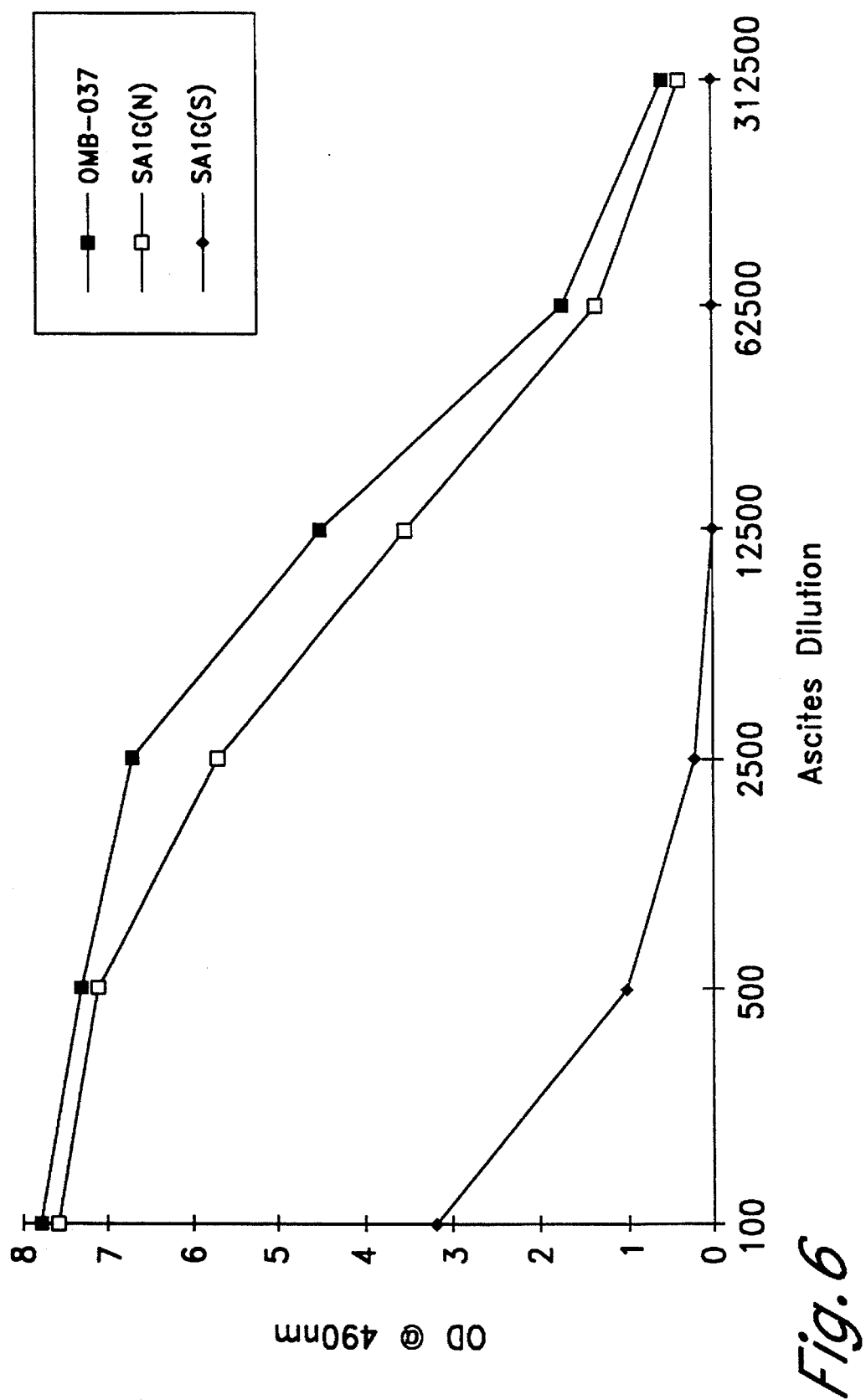
FIG. 6 illustrates the results of an ELISA to test for the presence of mouse immunoglobulin in ascites fluid obtained from the heterohybridoma SA1G7-516.5 as compared with the fusion partner OMB-037. (N) and (S) denote immunoglobulin produced in nude or SCID mice respectively.
Figure 7:
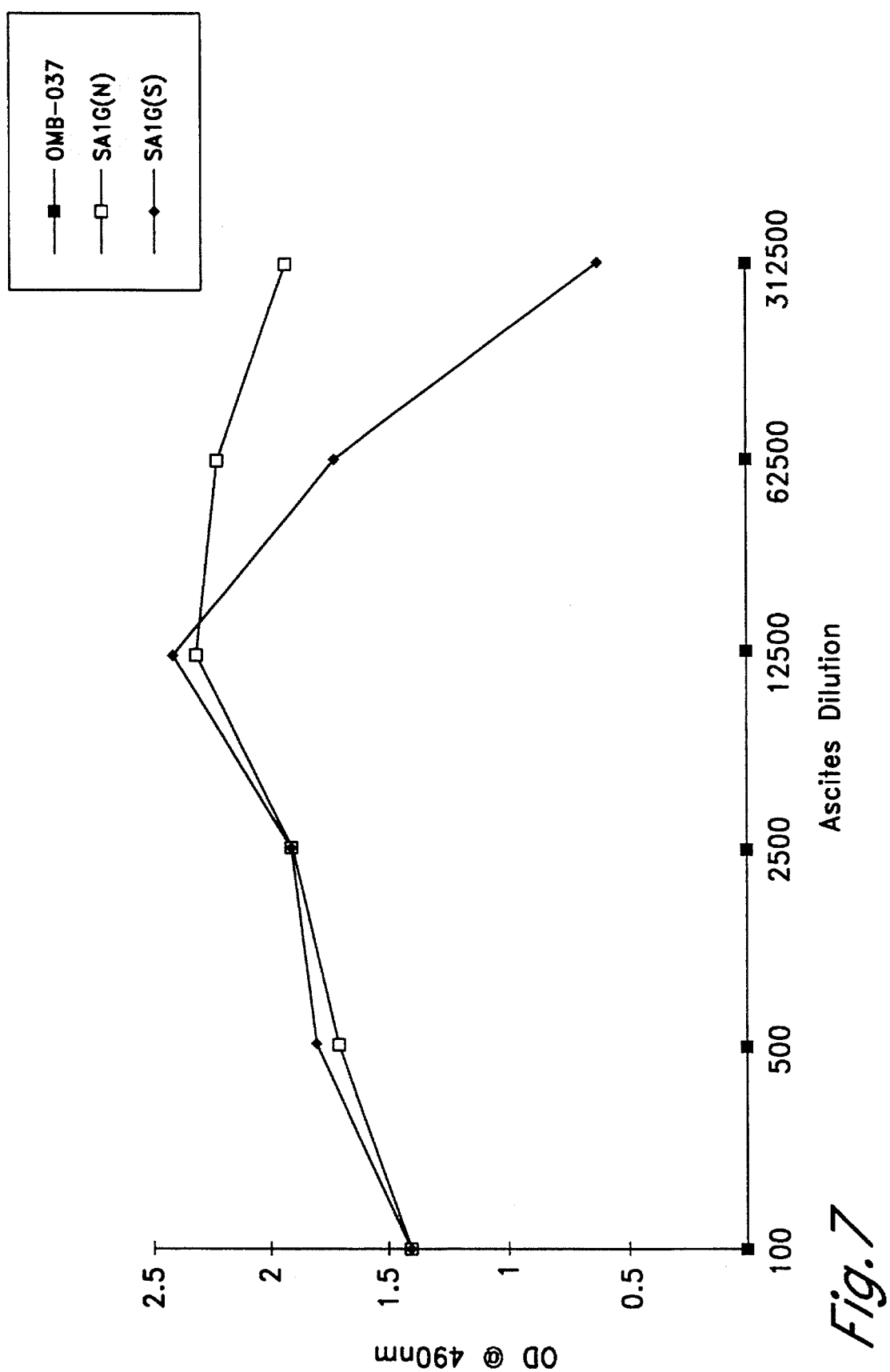
FIG. 7 illustrates the results of an ELISA to test for the presence of rabbit antibodies recognizing Group A Streptococcus as compared with fusion partner OMB-037. (N) and (S) denote immunoglobulin produced in nude or SCID mice respectively.
Figure 8:
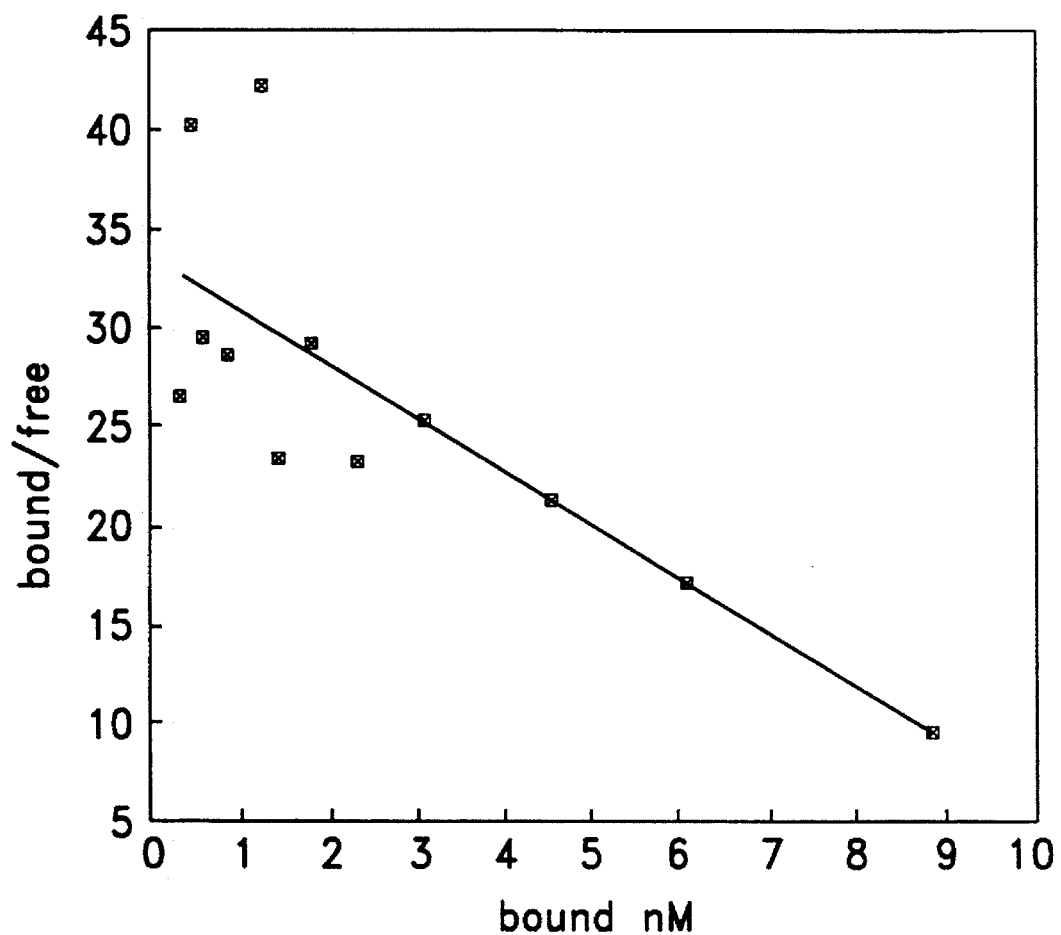
FIG. 8 is a $K_a$ plot for antibodies produced from heterohybridoma SA1G7-516.5.

Ascites characterization: Ascites from both nude and SCID mice were run in an antigen-specific assay (GAS antigen coated down) and both sources appeared to have good anti-Group A Streptococcus activity (FIG. 7). To determine the origin of the antibodies (host versus fusion partner), assays were run to detect rabbit immunoglobulin (FIG. 5) and mouse immunoglobulin (FIG. 6). In the mouse and rabbit species specific assays, the capture antibodies (either goat anti-rabbit or goat anti-mouse) were coated onto the plate to capture the appropriate species of antibody in the ascites. The captured antibodies were detected using goat anti-species antibodies conjugated to HRP. The results indicated that the ascites from both nude and SCID mice contained high amounts of rabbit antibodies (FIG. 5). Conversely, only ascites from nude mice contained high amounts of host antibodies (FIG. 6). These results also confirm that xenogeneic fusion partner OMB-037 did not produce antibody.

In our hands, the heterohybrid, SA1G7-516.5, produced at least 1 mg/ml of purified antibodies from ascites. The total volume of ascites produced per mouse was variable and ranged from 1–6 mls/mouse.

EXAMPLE 9

Rabbit Monoclonal Antibody Purification

Ascites fluid from the rabbit×mouse×rabbit heterohybrids grown in nude or SCID mice were clarified of proteins using a single salt cut with saturated ammonium sulfate. Lipoproteins were removed using dextran sulfate precipitation and rabbit immunoglobulin was purified by either of two different methods. In the first method, rabbit immunoglobulin was purified by ion exchange chromatography The buffer of the clarified ascites was exchanged with load/wash buffer (20 mM Tris, pH 8.0) in an Amicon Centriprep-30 column (Amicon, Beverly, Mass.) and loaded onto a Q Sepharose Fast Flow column (FFQ; Pharmacia) and eluted with a gradient buffer of 20 mM Tris, 0.5M NaCl, pH 8.0. Appropriate fractions were pooled for testing. In the second method, the clarified ascites was purified by immunoaffinity chromatography using an N-acetyl glucosamine (NAG)—agarose column (Sigma, St. Louis, Mo.). The loaded column was washed with phosphate buffered saline (PBS) and the rabbit anti-Group A Streptococcus antibodies were eluted with 10% N-acetyl glucosamine (Sigma) and dialyzed with PBS. Appropriate fractions were pooled for testing. All samples were tested for species identity (rabbit or mouse) as described in association with FIGS. 4 and 5. Antigen specificity was confirmed by ELISA (see Example 6 and the discussion associated with Table 1). Rabbit antibody fractions were pooled and any remaining murine immunoglobulin was removed using sheep anti-mouse immunoglobulin-coated polystyrene beads.

EXAMPLE 10

Use of Rabbit Monoclonal Antibodies and Rabbit Polyclonal Antibodies in Solid-phase Immunoassays Detecting Antibody Preparation:

In this Example, Rabbit monoclonal antibody SA1G7-516.5 was used as the detecting antibody for Group A Streptococcus in a solid phase immunoassay. 10 mg of the monoclonal antibody preparation was labeled with 10 mg of alkaline phosphatase. The conjugation of the alkaline phosphatase to the monoclonal antibodies followed procedures well known in the art of immunology. Both the antibodies and the alkaline phosphatase (AP) were dialyzed in PBS and filtered through 0.45 μm filters. The concentrations of the antibodies and AP were determined on a spectrophotometer at $A_{280}$. The antibody solution was diluted by weight to 5 mg/ml in PBS. It is contemplated that this procedure could be used for either monoclonal or polyclonal antibodies and that the methods could similarly be used with antibodies recognizing any number of antigen.

The AP was conjugated to the heterobifunctional reagent Succinimidyl 4-(N-maleimidomethyl)cyclohexane-1-carboxylate (SMCC, Pierce, Rockford, Ill.) using a 10:1 initial molar ratio of SMCC to AP. SMCC was suspended in dry acetonitrile to a concentration of 10 mg/ml. The SMCC and AP were combined under Argon and incubated for 30 mn at room temperature. The mixture was applied to a Sephadex G-25 column, saturated with Argon gas, to separate free from bound enzyme. The concentration of conjugated AP (SMCC-AP) was determined by spectrophotometer at $A_{280}$.

Rabbit monoclonal antibodies were conjugated to the heterobifunctional reagent N-Succinimidyl 3-(2-pyridyldithio)propionate (SPDP, Pierce). SPDP was also resuspended in dry Acetonitrile. The concentration of SPDP was determined at $A_{260}$. SPDP was mixed with the monoclonal antibodies at a molar ratio of 20:1 and incubated for 30 mn at room temperature under Argon. A 0.10 ml Dithiothreitol (DTT) solution was added to the antibody-SPDP mixture to give a final concentration of 1 mM DTT. Following a 30 mn incubation at room temperature, the conjugated antibodies were separated from unlabelled antibodies and free SPDP on a Sephadex G-25 column. The concentration of conjugated antibodies was determined at $A_{280}$.

The SMCC-AP and the SPDP-antibodies were separately diluted by weight to 1.5 mg/ml with PBS. Equal volumes of SMCC-AP and SPDP-antibodies were mixed and deoxygenated under Argon. The antibody and enzyme solutions were mixed and stirred for 90 mn at room temperature. Unreacted SPDP groups were blocked using a 125 mg/ml solution of N-ethlmaleimide (NEM, Pierce) to yield a final concentration in the reaction of 0.01 NEM/ml reaction solution. Unreacted SMCC groups were blocked using an equal volume of 0.20M 2-mercaptoethanol. The AP-rabbit monoclonal antibody conjugate was concentrated on a Centricor 30 column (Amicon) at 2° C.–8° C. to no greater than 25 mg/ml. The conjugated antibodies were dialyzed in PBS and purified by column chromatography. Peak fractions were pooled and the conjugated antibodies were diluted to 20 mA where 1 mA is equivalent to $A_{280}=0.001$.

Capture Antibody Preparation:

Rabbit monoclonal antibodies or rabbit polyclonal antibodies to Group A Streptococcus were coated onto latex beads as capture antibody. To prepare 0.36 ml. of coating solution, 0.012 ml of a 7.65 mg/ml stock antibody solution was combined with 0.309 ml coating buffer (50 mM ethanolamine in 0.9% NaCl pH 10.0) and 0.036 ml latex and incubated overnight at 45° C. 0.309 ml of backcoating buffer (0.3% bovine serum albumin in PBS) was added to the mixture and incubated for 2 hr. at room temperature. The labeled latex was spun down and resuspended in 0.5 ml PBS and stabilization buffer (10% sucrose, 2% nonfat dry milk in PBS) was added to obtain a final volume of 10 ml.

Solid-phase Immunoassay:

For an immunoassay to Group A Streptococcus, 3µl of the Group A Streptococcus antibody-latex solution as a 0.30% latex solid solution was spotted onto porous membranes such as those disclosed in U.S. Pat. No. 4,727,019. In this example POREX® (a porous polyethylene material, Porex Technologies, Atlanta, Ga.) filters were spotted with the Group A Streptococcus solution, as well as the positive and negative controls. An equal volume of Streptococcus-specific antibody conjugated to latex and preincubated with nitrous acid extract of Streptococcus was spotted in a second location to as a positive control. Purified Streptococcus-negative rabbit polyclonal antibody was spotted onto a third position on the porous membrane as a negative control.

Group A Streptococcus nitrous acid extracts or extracts from other organisms were prepared using methods disclosed in Example 6 and neutralized with potassium phosphate. 20µl of a solution, equivalent to $4\times10^6$ CFU/ml, was added to 1 drop of antibody conjugated to alkaline phosphatase. The sample was filtered through a 0.2µm filter and the total sample was applied to the porous member. Once the liquid passed through the porous member, the surface was washed with wash solution (1% Triton X-100, 0.002% Nitroblue Tetrazolium (wt/vol), and sodium azide in PBS). Detection of bound sample was determined by the addition of the AP substrate, indoxyl phosphate, in PBS (6.66 gm Tris, 0.956 ml of a 90% solution of 2-amino-2,methyl-1, propanol, 1 gm NaCl gm. sodium Azide, 0.290 gm indoxyl phosphate and 0.411 ml conc. HCl). A purple dot at the positive control position indicated that the correct technique was used and that the reagents were functional. A purple dot in the negative control position indicated that the sample did not contain human anti-rabbit antibody. A purple dot in the latex bound anti-Group A Streptococcus position indicated the presence of Group A Streptococcus in the test sample.

While particular embodiments of the invention have been described in detail, it will be apparent to those skilled in the art that these embodiments are exemplary rather than limiting, and the true scope of the invention is that defined in the following claims.

We claim:

1. A rabbit-mouse fusion partner having the ATCC accession number CRL 11086, said fusion partner producing undetectable levels of antibody as determined by an enzyme linked immunosorbent assay.

* * * * *

UNITED STATES PATENT AND TRADEMARK OFFICE
CERTIFICATE OF CORRECTION

PATENT NO. : 5,472,868
DATED : December 5, 1995
INVENTOR(S) : Robert T. McCormack, Ru-shya Liu, Joseph V. Manetta, John R. Sportsman It is certified that error appears in the above-indentified patent and that said Letters Patent is hereby corrected as shown below:

On title page, item [73], change "Eli Lilly & Company, Indianapolis, Ind." to --Eli Lilly & Company, Indianapolis, Ind.; and Hybritech, Incorporated, San Diego, Ca.--

Signed and Sealed this

Twenty-fifth Day of June, 1996

Attest:

BRUCE LEHMAN

*Attesting Officer*  *Commissioner of Patents and Trademarks*